United States Patent [19]

Mueller et al.

[11] Patent Number: 5,256,666
[45] Date of Patent: Oct. 26, 1993

[54] 3-ISOXAZOLYLPHENYL COMPOUNDS, THEIR PREPARATION AND THEIR USE

[75] Inventors: Stefan Mueller, Speyer; Hans Theobald, Limburgerhof; Harald Rang, Ludwigshafen; Volker Harries, Frankenthal, all of Fed. Rep. of Germany

[73] Assignee: BASF Aktiengesellschaft, Ludwigshafen, Fed. Rep. of Germany

[21] Appl. No.: 975,733

[22] Filed: Nov. 13, 1992

[30] Foreign Application Priority Data

Nov. 18, 1991 [DE] Fed. Rep. of Germany ....... 4137940

[51] Int. Cl.$^5$ ............... A01N 43/54; A01N 43/80; C07D 231/12; C07D 231/16
[52] U.S. Cl. ................. 514/256; 514/269; 514/340; 514/378; 514/380; 548/110; 546/14; 544/229
[58] Field of Search ............ 548/110; 514/378, 380, 514/340, 256, 269; 546/14; 544/229

[56] References Cited

U.S. PATENT DOCUMENTS 4,775,664  10/1988  Schubert et al. ............ 514/63

FOREIGN PATENT DOCUMENTS 3604781  8/1987  Fed. Rep. of Germany ........ 514/63

OTHER PUBLICATIONS

CA 10(11):95066c Asymmetric induction . . . silanes, Curran et al., p. 691, 1989.

*Primary Examiner*—Mary C. Lee
*Assistant Examiner*—Joseph K. McKane
*Attorney, Agent, or Firm*—Keil & Weinkauf

[57] ABSTRACT

3-Isoxazolylphenyl compounds Ia and Ib

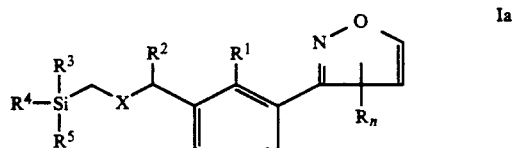

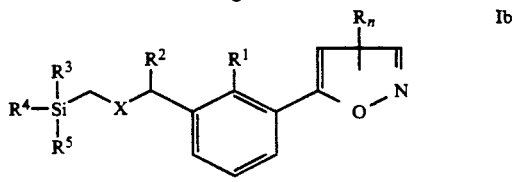

where
R is halogen; alkyl; haloalkyl; alkoxy; haloalkoxy; alkenyl; haloalkenyl; unsubstituted or substituted phenylethenyl; alkynyl; cycloalkyl; aryl; hetaryl; $CO_2R^6$ or $CONR^7R^8$,
$R^6$ is hydrogen, alkyl, cycloalkyl or benzyl;
$R^7$ and $R^8$ are each hydrogen, alkyl, cycloalkyl or benzyl or, together with the nitrogen atom to which they are bonded, form a heterocyclic radical;
n is 0, 1 or 2;
$R^1$ is halogen or alkyl;
$R^2$ is hydrogen; alkyl; alkenyl; alkynyl or cyano;
$R^3$ and $R^4$ independently of one another are each unsubstituted or substituted alkyl, alkenyl, cycloalkyl, phenyl, naphthyl, pyridyl or pyrimidinyl; or $R^3$ and $R^4$ together form unsubstituted or substituted alkylene;
$R^5$ is hydrogen; unsubstituted or substituted alkyl or one of the groups stated for $R^3$;
X is $CH_2$, O, S or $NR^9$ and
$R^9$ is hydrogen, alkyl, cycloalkyl, alkenyl, alkynyl or unsubstituted or substituted benzyl, processes for their preparation, agents containing them and the use thereof.

8 Claims, No Drawings

3-ISOXAZOLYLPHENYL COMPOUNDS, THEIR PREPARATION AND THEIR USE

The present invention relates to 3-isoxazolylphenyl compounds of the general formulae Ia and Ib

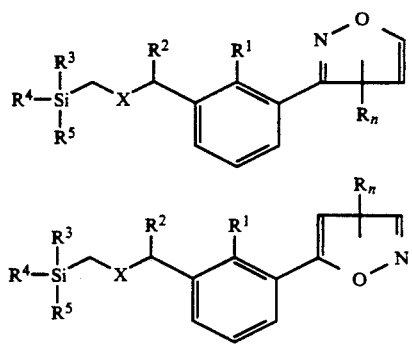

where

R is halogen; $C_1$-$C_4$-alkyl; $C_1$-$C_4$-haloalkyl; $C_1$-$C_4$-alkoxy; $C_1$-$C_4$-haloalkoxy; $C_2$-$C_4$-alkenyl; $C_2$-$C_4$-haloalkenyl; phenylethenyl which may carry from one to five halogen atoms;

$C_2$-$C_4$-alkynyl; $C_3$-$C_8$-cycloalkyl; aryl; hetaryl; $CO_2R^6$ or $CONR^7R^8$, where $R^6$ is hydrogen, $C_1$-$C_6$-alkyl, $C_3$-$C_6$-cycloalkyl or benzyl and $R^7$ and $R^8$ independently of one another are each hydrogen, $C_1$-$C_6$-alkyl, $C_3$-$C_6$-cycloalkyl or benzyl or, together with the nitrogen atom to which they are bonded, form a 3-membered to 8-membered, saturated or monounsaturated or diunsaturated heterocyclic radical consisting of carbon ring members, where this cyclic structure may furthermore contain one or two further hetero atoms selected from the group consisting of oxygen, sulfur and nitrogen;

n is 0, 1 or 2, and the radicals R may be different when n is 2;

$R^1$ is halogen or $C_1$-$C_4$-alkyl;

$R^2$ is hydrogen; $C_1$-$C_4$-alkyl; $C_2$-$C_4$-alkenyl; $C_2$-$C_4$-alkynyl or cyano;

$R^3$ and $R^4$ independently of one another are each $C_1$-$C_4$-alkyl or $C_2$-$C_8$-alkenyl, where these radicals may carry from one to nine halogen atoms and/or one of the following groups: $C_3$-$C_8$-cycloalkyl, $C_1$-$C_4$-alkoxy, $C_1$-$C_4$-haloalkoxy, $C_1$-$C_4$-alkylthio, $C_1$-$C_4$-haloalkylthio, phenyl, phenoxy and phenylthio, and the aromatic groups in turn may carry from one to five halogen atoms and/or from one to three of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

$C_3$-$C_8$-cycloalkyl which may carry from one to three of the following groups: halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

phenyl, naphthyl, pyridyl or pyrimidyl, where the aromatic radicals may carry from one to seven halogen atoms and/or from one to four of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

or $R^3$ and $R^4$ together form $C_2$-$C_5$-alkylene which may carry from one to three $C_1$-$C_3$-alkyl groups;

$R^5$ is hydrogen;

$C_5$-$C_{18}$-alkyl which may carry from one to nine halogen atoms and/or one of the following groups: $C_3$-$C_8$-cycloalkyl, $C_1$-$C_4$-alkoxy, $C_1$-$C_4$-haloalkoxy, $C_1$-$C_4$-alkylthio, $C_1$-$C_4$-haloalkylthio, phenyl, phenoxy and phenylthio, where the aromatic groups in turn may carry from one to five halogen atoms and/or from one to three of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

or one of the groups stated for $R^3$;

X is $CH_2$, O, S or $NR^9$, where $R^9$ is hydrogen, $C_1$-$C_4$-alkyl, $C_3$-$C_6$-cycloalkyl, $C_2$-$C_4$-alkenyl, $C_2$-$C_4$-alkynyl or benzyl, and the benzyl radical in turn may carry from one to five halogen atoms and/or from one to three of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio.

The present invention furthermore relates to processes for the preparation of these compounds, pesticides which contain these compounds as active ingredients and methods for controlling pests.

It is known that certain silane derivatives are effective against pests (EP-A 224 024, DE-A 36 04 781). However, the action of these known compounds is unsatisfactory.

It is an object of the present invention to provide novel compounds having improved properties with regard to the biological activity.

We have found that this object is achieved by the 3-isoxazolylphenyl compounds defined at the outset. We have also found processes for their preparation, agents containing them, and their use for controlling pests.

The compounds Ia and Ib are obtainable by various synthesis methods known in principle from the literature. They are advantageously obtained by one of the processes A to G described below.

Process A

The 3-isoxazolylphenyl compounds of the general formulae Ia and Ib are obtained, for example, by reacting a silane of the general formula II in a conventional manner (Houben-Weyl, Vol. 13/5, page 54), in an inert organic solvent, with a compound of the general formula IIIa or IIIb.

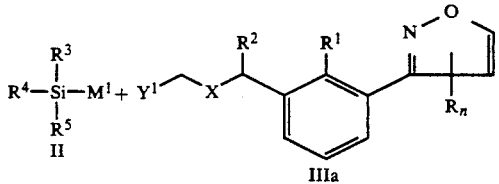

or

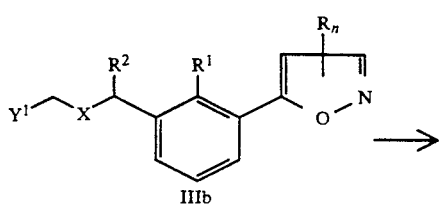

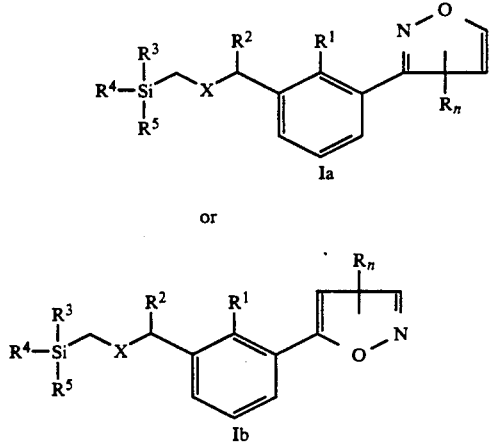

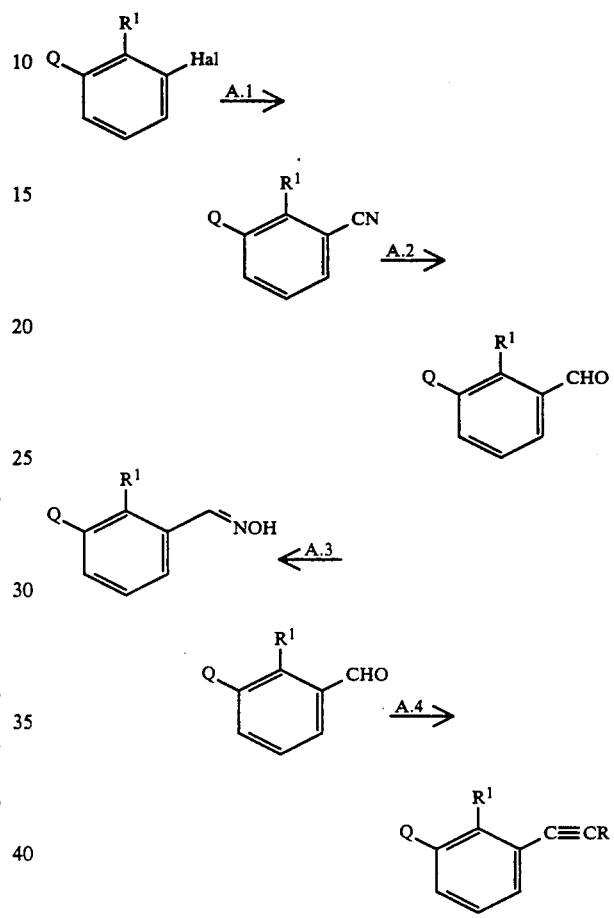

In the formula II, $M^1$ is one equivalent of an alkali metal or alkaline earth metal ion, such as Li+, Na+, K+, ½ Mg$^{2+}$ and ½ Ca$^{2+}$, preferably Li+ or ½ Mg$^{2+}$.

In formulae IIIa and IIIb, $Y^1$ is a nucleofugic leaving group, such as halogen, for example fluorine, chlorine, bromine or iodine, in particular chlorine or bromine, or sulfonate, such as $C_1$-$C_4$-alkanesulfonate, or phenylsulfonate which is unsubstituted or substituted in the aryl moiety, in particular methanesulfonate or 4-methylphenylsulfonate.

This reaction is usually carried out at from $-120$ to $100°$ C., preferably from $-78°$ to $50°$ C.

Suitable solvents are aliphatic hydrocarbons, such as pentane, hexane, cyclohexane and petroleum ether, aromatic hydrocarbons, such as benzene, toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, and dimethyl sulfoxide, particularly preferably tetrahydrofuran and diethyl ether.

It is also possible to use mixtures of the stated solvent.

The starting materials are generally reacted with one another in equimolar amounts. It may be advantageous for the yield to use the silane II in an excess or in less than the stoichiometric amount, based on the compound IIIa or IIIb.

In a modification of the process A described above, the compounds of the general formulae Ia and Ib are also obtained if a compound whose substituent in the 3-position can readily be converted in a subsequent reaction stage into the corresponding isoxazolyl radical is used instead of the compounds IIIa or IIIb substituted by isoxazolyl in the 3-position.

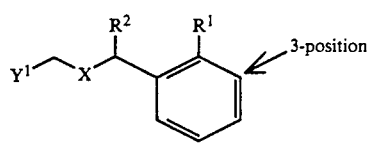

Compounds which are particularly suitable in this respect are those in which the substituent in the 3-position has one of the following meanings: halogen (Hal), in particular chlorine, bromine or iodine, cyano, formyl, —CH=NOH or ethynyl (unsubstituted or substituted by a radical R).

The conversion of the substituent is carried out by the following reaction scheme according to the literature subsequently cited. For the sake of clarity, the group $Y^1CH_2XCHR^2$— is denoted by Q.

Stage A.1: J. March, Advanced Organic Chemistry 1977, page 603

Stage A.2: J. March, Advanced Organic Chemistry 1977, page 835

Stage A.3: J. March, Advanced Organic Chemistry 1977, page 825

Stage A.4: J. March, Advanced Organic Chemistry 1977, page 936 and Liebigs Ann. Chem. 1980, page 2061.

The conversion of the oximes or alkynes obtained by this reaction route into the corresponding isoxazolyl compounds is described after processes A to F.

Particularly suitable starting compounds in this process A in addition to the compounds IIIa and IIIb described at the outset are those derivatives in which the radical in the 3-position is chlorine or cyano.

Process B

3-Isoxazolylphenyl compounds of the general formulae Ia and Ib in which X is $CH_2$ are also obtained by reacting a silane of the general formula IV in a conventional manner (DE-A 38 28 926, EP-A 249 015, EP-A 224 024, Pest. Sci. 29 (1990), 215), in an inert organic solvent, with a compound of the general formula Va or Vb.

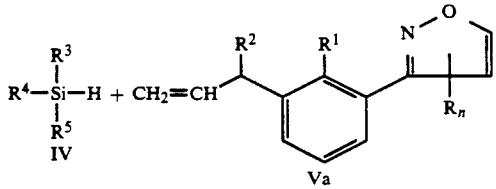

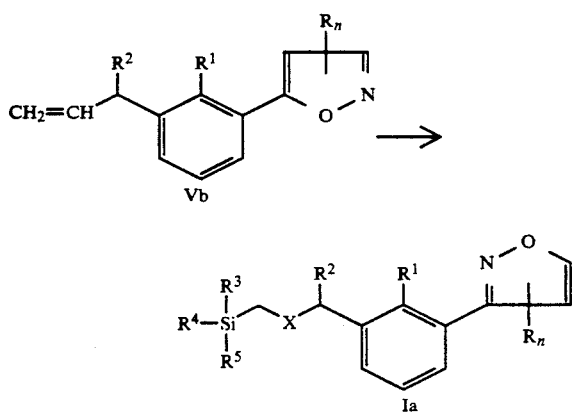

This reaction is usually carried out at from −120° to 100° C., preferably from −50° to 50° C.

Suitable solvents are aliphatic hydrocarbons, such as pentane, hexane, cyclohexane and petroleum ether, aromatic hydrocarbons, such as benzene, toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, alcohols, such as methanol, ethanol, n-propanol, isopropanol, n-butanol and tert-butanol, and dimethyl sulfoxide and dimethylformamide, particularly preferably cyclohexane and isopropanol.

Mixtures of the stated solvents may also be used.

In general, the reaction can be improved by using catalysts. Suitable catalysts are in general the slats or complexes of metals of subgroup VIII of the Periodic Table, catalysts as also used in the Ziegler-Natta synthesis and peroxides. Hexachloroplatinate and tris[triphenylphosphine]-rhodium chloride are particularly suitable.

The starting materials are generally reacted with one another in equimolar amounts. It may be advantageous for the yield to use the silane IV in an excess or in less than than the stochiometric amount, based on the compound Va or Vb.

In a modification of process B described above, the compounds of the general formulae Ia and Ib are also obtained if a compound whose substituent in the 3-position can be readily converted in a subsequent reaction stage into the corresponding isoxazolyl radical is used instead of the compounds Va or Vb substituted in the 3-position by isoxazolyl.

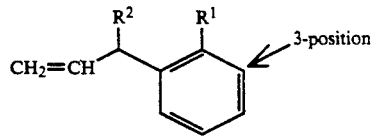

Compounds which are particularly suitable in this respect are those in which the substituent in the 3-position has one of the following meanings: halogen, in particular chlorine, bromine or iodine, cyano, formyl —CH=NOH or ethynyl (unsubstituted or substituted by a radical R).

The conversion of the substituent is carried out by the reaction scheme shown above for process A, according to the literature likewise cited there.

Particularly suitable starting compounds in this process B in addition to the compounds Va and Vb described at the outset are those derivatives in which the radical in the 3-position is chlorine or cyano.

Process C

In a further preparation process, 3-isoxazolylphenyl compounds of the general formulae Ia and Ib in which X is $CH_2$ are also obtained by reacting a silane of the general formula IV in a conventional manner (J. March, Advanced Organic Chemistry 2 Ed., McGraw Hill Ltd., 1977, pages 409–412), in an inert organic solvent, with a compound of the general formula VIIa or VIIb.

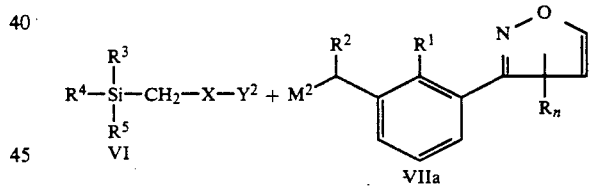

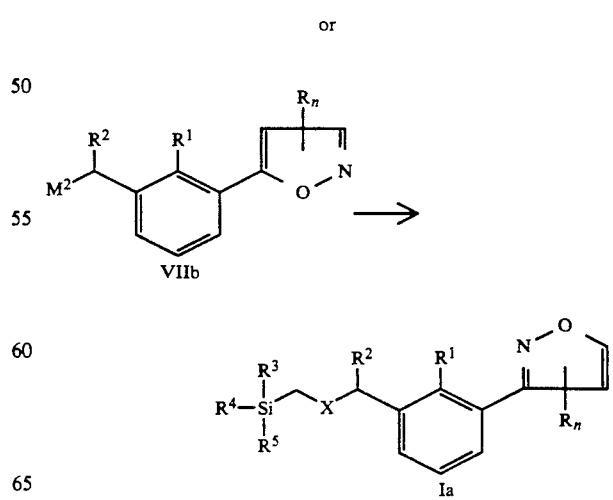

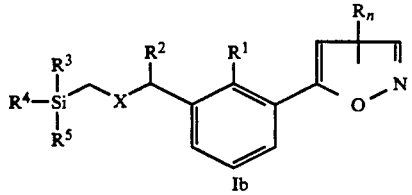

Ib

In the formula VI, $Y^2$ is a nucleofugic leaving group as stated in general and in particular for $Y^1$ in process A and X is $CH_2$.

In the formulae VIIa and VIIb, $M^2$ is one equivalent of an alkali metal or alkaline earth metal ion as stated in general for $M^1$ in process A.

This reaction is usually carried out at from $-120°$ to $100°$ C., preferably from $-78°$ to $50°$ C.

Suitable solvents are aliphatic hydrocarbons, such as pentane, hexane, cyclohexane and petroleum ether, aromatic hydrocarbons, such as benzene, toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, and dimethyl sulfoxide, particularly preferably tetrahydrofuran and diethyl ether.

Mixtures of the stated solvents may also be used.

In general, the reaction can be improved by using catalytic amounts of copper(I) or copper(II) salts.

The starting materials are generally reacted with one another in equimolar amounts. It may be advantageous for the yield to use the silane VI in an excess or in less than the stoichiometric amount, based on VIIa or VIIb.

In a modification of process C described above, the compounds of the general formulae Ia and Ib are also obtained if a compound whose substituent in the 3-position can be readily converted in a subsequent reaction stage into the corresponding isoxazolyl radical is used instead of the compounds VIIIa substituted in the 3-position by isoxazolyl.

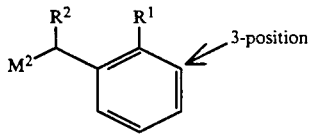

Compounds which are particularly suitable in this respect are those in which the substituent in the 3-position has one of the following meanings: halogen, in particular chlorine, bromine or iodine, cyano, formyl, —CH=NOH or ethynyl (unsubstituted or substituted by a radical R).

The conversion of the substituent is carried out by the reaction scheme shown above for process A, according to the literature likewise cited there.

Particularly suitable starting compounds in this process C in addition to the compounds VIIa and VIIb described at the outset are those derivatives in which the radical in the 3-position is chlorine or cyano.

Process D

The 3-isoxazolylphenyl compounds of the general formulae Ia and Ib in which X is $CH_2$ are also obtained by reacting a silane of the general formula VIII in a conventional manner (Syn. Com. 17 (1987), 385), in an inert organic solvent, with a compound of the general formula IXa or IXb.

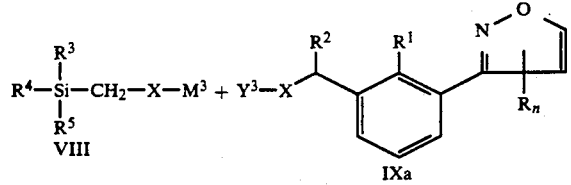

VIII or

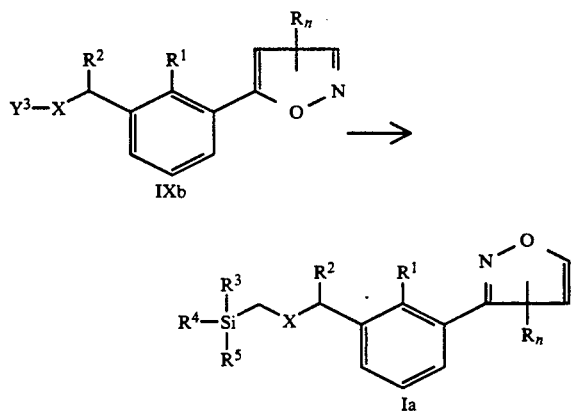

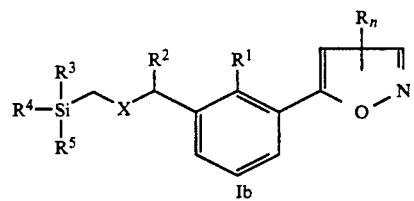

Ib

In the formula VIII, $M^3$ is one equivalent of an alkali metal or alkaline earth metal ion as stated in general for $M^1$ in process A.

In the formulae IXa and IXb, $Y^2$ is a nucleofugic leaving group as stated in general and in particular for $Y^1$ in process A and X, is $CH_2$.

The reaction is usually carried out at from $-120°$ to $100°$ C., preferably from $-78°$ to $40°$ C.

Suitable solvents are aliphatic hydrocarbons, such as pentane, hexane, cyclohexane and petroleum ether, aromatic hydrocarbons, such as benzene, toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, and dimethyl sulfoxide, particularly preferably tetrahydrofuran and diethyl ether.

Mixtures of the stated solvents may also be used.

The starting materials are generally reacted with one another in equimolar amounts. It may be advantageous for the yield to use the silane VIII in an excess or in less than the stoichiometric amount, based on IXa or IXb.

In a modification of process D described above, the compounds of the general formulae Ia and Ib are also obtained if a compound whose substituent in the 3-position can be readily converted in a subsequent reaction stage into the corresponding isoxazolyl radical is used instead of the compounds IXa or IXb substituted in the 3-position by isoxazolyl.

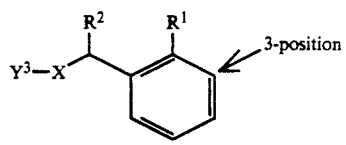

Compounds which are particularly suitable in this respect are those in which the substituent in the 3-position has one of the following meanings: halogen, in particular chlorine, bromine or iodine, cyano, formyl, —CH=NOH or ethynyl (unsubstituted or substituted by a radical R).

The conversion of the substituent is carried out by the reaction scheme shown above for process A, according to the literature likewise cited there.

Particularly suitable starting compounds in this process D in addition to the compounds IXa and IXb described at the outset are those derivatives in which the radical in the 3-position is chlorine or cyano.

Process E

The 3-isoxazolylphenyl compounds of the general formulae Ia and Ib in which X is $CH_2$ are also obtained, for example, by reacting a silane of the general formula X in a conventional manner (DE-A 36 04 781, DE-A 38 23 979, EP-A 249 015, EP-A 224 024), in an inert organic solvent, with a compound of the general formula XIa or XIb.

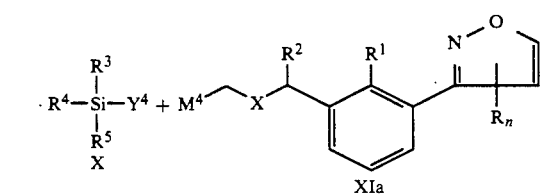

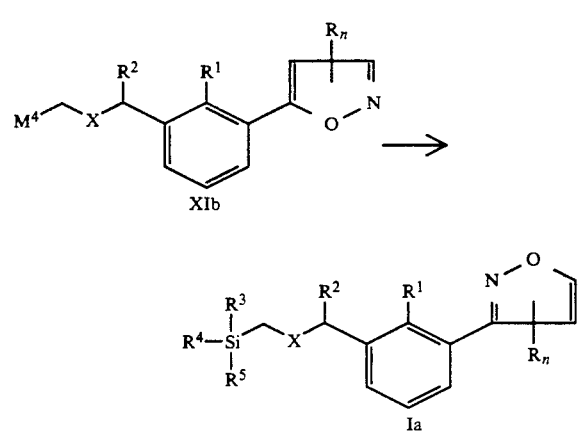

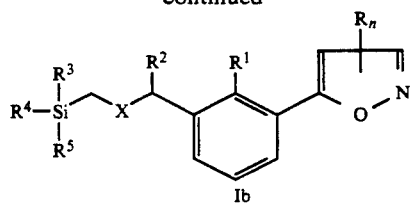

In the formula X, $Y^4$ is a nucleofugic leaving group as stated in general and in particular for $Y^1$ in process A.

In the formulae XIa and XIb, $M^4$ is one equivalent of an alkali metal or alkaline earth metal ion as stated in general for $M^1$ in process A.

The reaction is usually carried out at from $-120°$ to $100°$ C., preferably from $-78°$ to $0°$ C.

Suitable solvents are aliphatic hydrocarbons, such as pentane, hexane, cyclohexane and petroleum ether, aromatic hydrocarbons, such as benzene, toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, and dimethyl sulfoxide, particularly preferably tetrahydrofuran and diethyl ether.

Mixtures of the stated solvents may also be used.

The starting materials are reacted with one another in general in equimolar amounts. It may be advantageous for the yield to use the silane X in an excess or in less than the stoichiometric amount, based on XIa or XIb.

In a modification of process E described above, the compounds of the general formulae Ia and Ib are also obtained if a compound whose substituent in the 3-position can readily be converted in a subsequent reaction stage into the corresponding isoxazolyl radical is used instead of the compounds XIa or XIb substituted in the 3-position by isoxazolyl.

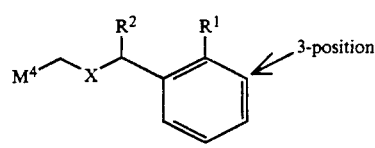

Compounds which are particularly suitable in this respect are those in which the substituent in the 3-position has one of the following meanings: halogen, in particular chlorine, bromine or iodine, cyano, formyl, —CH=NOH or ethynyl (unsubstituted or substituted by a radical R).

The conversion of the substituent is carried out by the reaction scheme shown above for process A, according to the literature likewise cited there.

Particularly suitable starting compounds in this process E in addition to the compounds XIa and XIb described at the outset are those derivatives in which the radical in the 3-position is chlorine or cyano.

Process F

The 3-isoxazolylphenyl compounds of the general formulae Ia and Ib in which X is not $CH_2$ are also obtained by reacting a silane of the general formula XII in a conventional manner (EP-A 202 893), in an inert organic solvent, with a compound of the general formula XIIIa or XIIIb.

instead of the compounds XIIIa or XIIIb substituted in the 3-position by isoxazolyl.

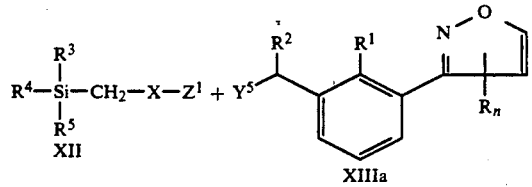

Compounds which are particularly suitable in this respect are those in which the substituent in the 3-position has one of the following meanings: halogen, in particular chlorine, bromine or iodine, cyano, formyl, —CH=NOH or ethynyl (unsubstituted or substituted by a radical R).

The conversion of the substituent is carried out by the reaction scheme shown above for process A, according to the literature likewise cited there.

Particularly suitable starting compounds in this process F in addition to the compounds XIIIa and XIIIb described at the outset are those derivatives in which the radical in the 3-position is chlorine, cyano or formyl.

Process G

The 3-isoxazolylphenyl compounds of the general formulae Ia and Ib in which X is not $CH_2$ are also obtained by reacting a silane of the general formula XIV in a conventional manner (U.S. Pat. No. 2,572,402, DE-A 38 05 117), in an inert organic solvent, with a compound of the general formula XVa or XVb.

In the formulae XIIIa and XIIIb, $Y^5$ is a nucleofugic leaving group as stated in general and in particular for $Y^1$ in process A.

In the formula XII, $Z^1$ is hydrogen or one equivalent of an alkali metal or alkaline earth metal ion as stated in general for $M^1$ in process A.

The reaction is usually carried out at from $-120°$ to $100°$ C., preferably from $-78°$ to $50°$ C.

Suitable solvents are aliphatic hydrocarbons, such as pentane, hexane, cyclohexane and petroleum ether, aromatic hydrocarbons, such as benzene, toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tertbutyl methyl ketone, and dimethyl sulfoxide and dimethylformamide, particularly preferably tetrahydrofuran and diethyl ether.

Mixtures of the stated solvents may also be used.

The starting materials are reacted with one another in general in equimolar amounts. It may be advantageous for the yield to use the silane XII in an excess or in less than the stoichiometric amount, based on XIIIa or XIIIb.

In a modification of process F described above, the compounds of the general formulae Ia and Ib are also obtained if a compound whose substituent in the 3-position can be readily converted in a subsequent reaction stage into the corresponding isoxazolyl radical is used -continued

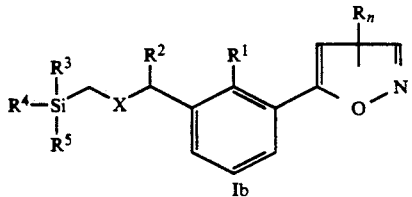

Ib

In the formula XIV, $Y^6$ is a nucleofugic leaving group as stated in general and in particular for $Y^1$ in process A.

In the formulae XVa and XVb, $Z^2$ is hydrogen or one equivalent of an alkali metal or alkaline earth metal ion as stated in general for $M^1$ in process A.

This reaction is usually carried out at from $-120°$ to $100°$ C., preferably from $-78°$ to $50°$ C.

Suitable solvents are aliphatic hydrocarbons, such as pentane, hexane, cyclohexane and petroleum ether, aromatic hydrocarbons, such as benzene, toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tertbutyl methyl ketone, and dimethyl sulfoxide and dimethylformamide, particularly preferably dimethylformamide and tert-butyl methyl ketone.

Mixtures of the stated solvents may also be used.

To improve the yields or to increase the reaction rate, it may be advantageous to carry out the reaction in the presence of a base.

Suitable bases are in general inorganic compounds, such as alkali metal and alkaline earth metal hydrides, such as lithium hydride, sodium hydride, potassium hydride and calcium hydride, alkali metal amides, such as lithium amide, sodium amide and potassium amide, organometallic compounds, in particular alkali metal organyls, such as methyllithium, butyllithium and phenyllithium, and alkylmagnesium halides, such as methylmagnesium chloride.

Sodium hydride, potassium hydride, sodium amide, methyllithium and butyllithium are particularly preferred.

The bases are used in general in equimolar amounts or in an excess of from 1 to 10 mol %, based on the starting material XIV.

The starting materials are generally reacted with one another in equimolar amounts. It may be advantageous for the yield to use the silane XIV in an excess or in less than the stoichiometric amount, based on XVa or XVb.

In a modification of process G described above, the compounds of the general formulae Ia and Ib are also obtained if a compound whose substituent in the 3-position can readily be converted in a subsequent reaction stage into the corresponding isoxazolyl radical is used instead of the compounds XVa or XVb substituted in the 3-position by isoxazolyl.

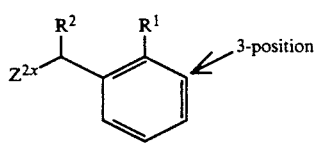

Compounds which are particularly suitable in this respect are those in which the substituent in the 3-position has one of the following meanings: halogen, in particular chlorine, bromine or iodine, cyano, formyl, $-CH=NOH$ or ethynyl (unsubstituted or substituted by a radical R).

The conversion of the substituent is carried out by the reaction scheme shown above for process A, according to the literature likewise cited there.

Particularly suitable starting compounds in this process G in addition to the compounds XVa and XVb described at the outset are those derivatives in which the radical in the 3-position is chlorine, cyano or formyl.

The preparation of the silanes of the general formulae II, IV, VI, VIII, XII and XIV which are required for the reactions described above is described in, for example, U.S. Pat. No. 4,775,664 (corresponding to EP-A 224 024) and in the literature cited there.

The intermediates of the general formulae IIIa or IIIb and XVa or XVb which are furthermore required and in which X is oxygen are obtainable by various routes.

For example, the compounds XVa ($Z^2=H$, $X=O$) are obtained by converting a protected 3-formylbenzyl alcohol of the general formula XVI in a conventional manner, in an inert organic solvent, in general in the presence of a base, into the corresponding oxime XVIIa, then subjecting XVIIa, in an inert organic solvent in the presence of an oxidizing agent and of a base, to an addition reaction with an alkyne of the formula XVIIIa, and eliminating the protective group from the resulting 3-isoxazolylbenzyl ether XIXa in a conventional manner in an inert organic solvent in the presence of an acid or of a catalyst.

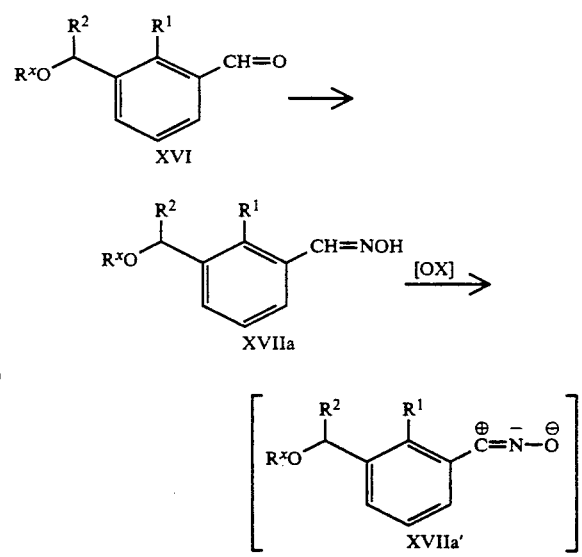

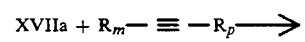

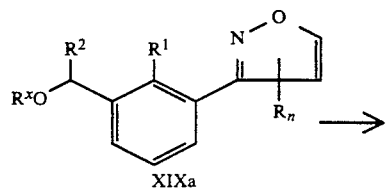

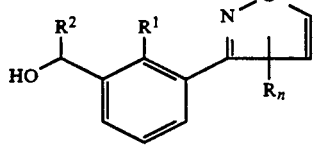

XV ($Z^2$ = H, X = O)

In the formulae XVI, XVIIa, XVIIa' and XIXa, $R^x$ is a protective group, such as methoxymethyl, 2-methoxyethoxymethyl, tetrahydro-2-pyranyl, tetrahydro-2-furanyl, tert-butyldimethylsilyl or trimethylsilyl.

In the formula XVIIIa, m and p are each 0 or 1, the sum m+p corresponding to the value of n.

The conversion of the aldehyde XVI into the oxime XVIIa is effected in a conventional manner (Houben-Weyl, Methoden der organischen Chemie, Vol. VII/1, page 471 et seq., Vol. X/4, page 56 et seq.).

The subsequent cleavage of the 3-isoxazolylbenzyl ether XIXa to give the 3-isoxazolylbenzyl alcohol is carried out in a conventional manner (T. Greene, Protective Groups in Organic Chemistry, J. Wiley & Sons, New York 1981; Tietze et al., Reaktionen und Synthesen, Georg-Thieme-Verlag 1981, page 363 et seq.) in a inert organic solvent in the presence of an acid or of a catalyst.

The required intermediates XVb are obtained in a similar manner by converting an ether-protected 3-formylbenzyl alcohol of the general formula XVI in a conventional manner in an inert organic solvent in the presence of a base by means of a phosphonium or phosphonate reagent into the corresponding 3-bromylvinyl derivative XX in a Wittig or Horner-Wittig reaction, then converting XX in an inert organic solvent in the presence of a base into an alkyne of the formula XVIIIb, which is then subjected in a conventional manner, in an inert organic solvent in the presence of an oxidizing agent and of a base, to an addition reaction with an oxime of the formula XVIIb to give the 3-isoxazolylbenzyl ether XIXb, from which the protective group is eliminated in the conventional manner.

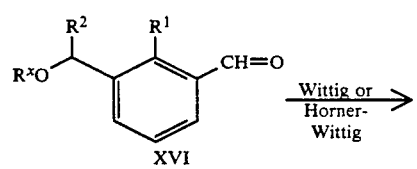

XVI → Wittig or Horner-Wittig

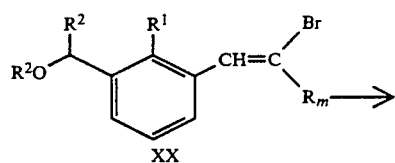

XX

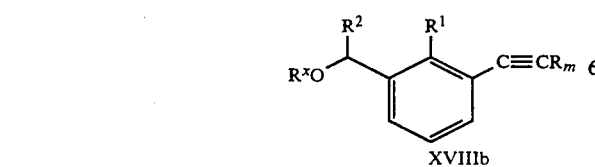

XVIIIb

XVIIIb + $R_p$—CH=NOH ⟶

XVIIb

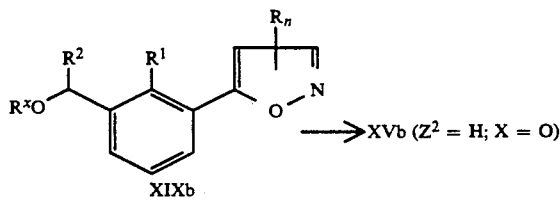

XIXb ⟶ XVb ($Z^2$ = H; X = O)

Preferred Wittig or Horner-Wittig reagents are the triphenylphosphonium halides and the diethyl phosphonates.

$R^x$ (formulae XVI, XVIIIb and XIXb), $R_m$ (formulae XX and XVIIIb) and $R_p$ (formula XVIIb) have the above-mentioned meanings.

The Wittig or Horner-Wittig reaction of the aldehyde XVI is carried out in a conventional manner (e.g. Liebigs Ann. Chem. 1980, page 2061 et seq.; Synthesis 1975, page 458 et seq.; DE-A 3 927 479).

The reaction of XVIIb with XVIIIb and the subsequent cleavage of the ether XIXb are carried out under conditions similar to those described above for the reaction of XVIIa with XVIIIa and for the cleavage of the ether XIXa.

The following reactions known from the literature are also particularly suitable for preparation of the 3-isoxazolylbenzyl alcohols XVb ($Z^2$=H), in which n is 0 or 1:

1. Similarly to Tietze et al., Reaktionen und Synthesen, Georg-Thieme Verlag 1981, page 299 et seq.

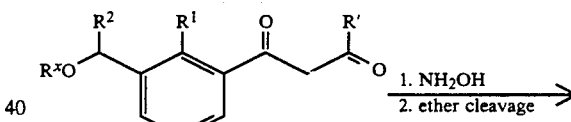

1. NH$_2$OH
2. ether cleavage

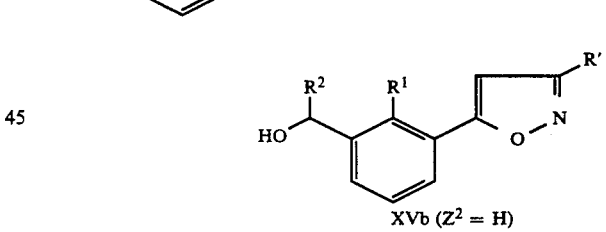

XVb ($Z^2$ = H)

(R' = Hydrogen or a radical R)

2. Similarly to Huisgen et al., Chem. Ber. 1973, page 3291 et seq.

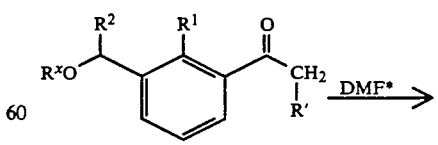

DMF*

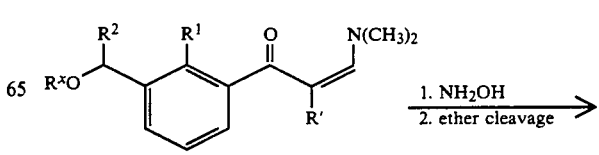

1. NH$_2$OH
2. ether cleavage

-continued

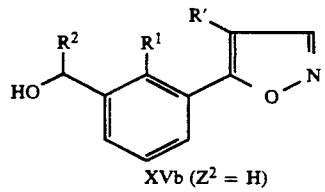

XVb ($Z^2$ = H)

*DMF = Dimethylformamide

3. Similarly to Bowden et al., J. Chem. Soc. 1946, page 953 et seq.

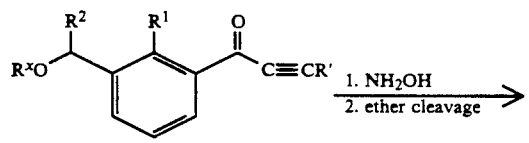

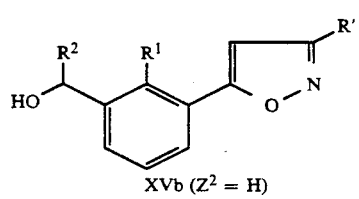

XVb ($Z^2$ = H)

The 3-formylbenzyl ether XVI required for the synthesis of the 3-isoxazolylbenzyl alcohols XVa and XVb is prepared by conventional methods (DE-A 3 927 479), according to the following reaction scheme:

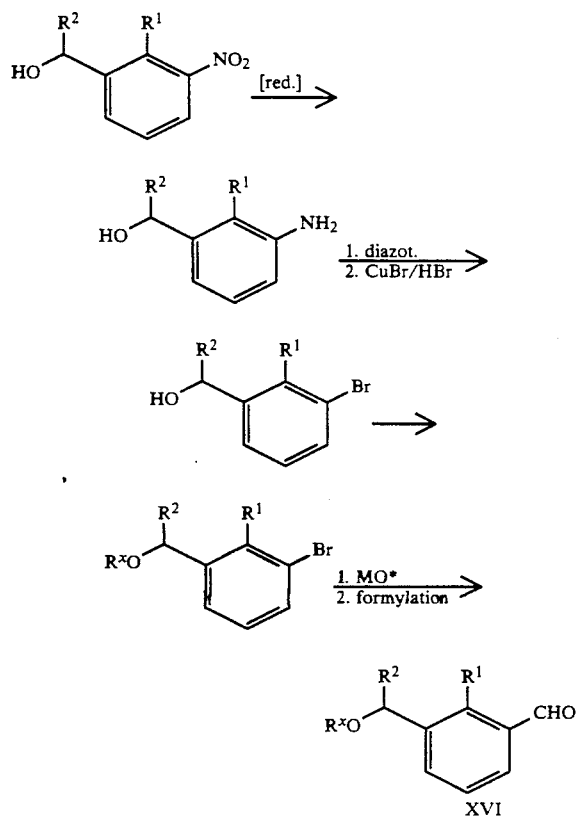

*MO = Metal or metal organyl

The reduction [Red.] in the diazotization [Diazot.] can be carried out by the methods described in EP-A 54 180.

The alcohol can be etherified by the method described by Tietze/Eicher (Reaktionen und Synthesen, Thieme Verlag, 1981, page 184).

The reaction of the corresponding organometallic compounds (Grignard compound or lithium organyl compound) with certain formamides, e.g. dimethylformamide, 1-formylpiperidine or 2-(formylmethylamino)-pyridine, is suitable for the preparation of the aldehyde XVI (cf. Houben-Weyl, Methoden der organischen Chemie, Volume E 3, page 130).

The benzyl alcohols of the general formula XVa or XVb where $R^2$ is cyano, $C_2$-$C_4$-alkynyl, $C_2$-$C_4$-alkenyl or $C_1$-$C_4$-alkyl are advantageously obtained by first oxidizing the unsubstituted benzyl alcohols in which $R^2$ is H to the corresponding benzaldehydes XXI.

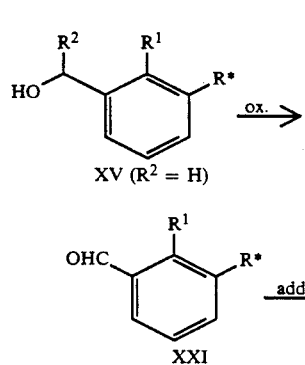

XV ($R^2$ = H)

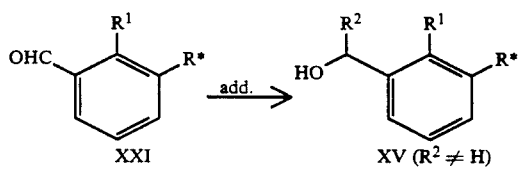

XXI      XV ($R^2 \ne$ H)

In the formulae XV and XXI, R* in this case is isoxazolyl. Suitable oxidizing agents are all conventional oxidizing agents which convert primary alcohols into aldehydes (Houben-Weyl, Methoden der organischen Chemie, Volume E3, page 265 et seq.). Compounds with transition metals in a relatively high oxidation state, for example pyridinium chlorochromate, are particularly suitable.

The benzaldehydes XXI can be converted into the substituted benzyl alcohols in which $R^2$ is not H in a conventional manner in a subsequent reaction step. Here, a) if $R^2$ is CN the benzaldehyde is reacted with hydrocyanic acid or with a metal cyanide in the presence or absence of an acid;

b) if $R^2$ is $C_2$-$C_4$-alkynyl, $C_2$-$C_4$-alkenyl or $C_2$-$C_4$-alkyl the benzaldehyde is reacted with a metal organyl $MR^2$ or $R^2MHal$, where M is an alkali metal, alkaline earth metal or transition metal and Hal is halogen.

For the preparation of the cyanohydrins, the benzaldehydes are reacted with hydrocyanic acid, with hydrocyanic acid used in situ from metal cyanides or with metal cyanides in the presence of an alkali metal bisulfite solution, if necessary basic catalysts, such as potassium carbonate, or phase transfer catalysts, eg. benzyltriethylammonium chloride, being added.

Preferably used metal cyanides are alkali metal cyanides, eg. sodium cyanide or potassium cyanide.

The reaction is carried out in a conventional manner, for example as described in Houben-Weyl, Methoden der organischen Chemie, Volume VIII, pages 274–278, 1952 edition, and Volume E5, page 1413 et seq., 1985.

Suitable metal organyls are the corresponding organometallic compounds, in particular lithium organyl compounds LiR², such as methyllithium, ethyllithium or butyllithium, or the corresponding Grignard compounds R²MgHal, where Hal is chlorine, bromine or iodine, eg. methylmagnesium bromide, ethylmagnesium bromide, propylmagnesium iodide or vinylmagnesium iodide.

The reaction with metal organyls can be carried out in a conventional manner, for example as described in Houben-Weyl, Methoden der org. Chemie, Volume 13/2a, page 285 et seq., 1973, in an inert organic solvent, such as ether or tetrahydrofuran, under an inert gas, so that further information in this context is unnecessary.

The corresponding chloromethyl ethers of the type III (X=O, Y¹=Cl) can be prepared by reacting benzyl alcohols of the type XV (Z²=H, X=O) with trioxane and trimethylsilyl chloride (A. Skipov et al., J. Gen. Chem. 1989, 1067).

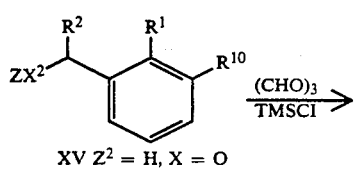

Further processes for the preparation of III (Y¹=Cl, Br or I, X=O) are described in Houben-Weyl, Volume VI/3, page 119.

The halomethyl ethers of the type III (Y¹=Cl, Br or I, X=O) can be converted according to Houben-Weyl, Volume 13/2a, page 114 or R. Tacke (Zeitschr. f. Naturforsch. B 1983, 738) or E. Corey (Tetrahedron Lett. 24 (1983), 3163) into corresponding metallized derivatives of the type XI (M⁴=Li, Na, K or Mg, X=O), which are reacted, either after isolation and/or purification or in situ, with electrophiles of the type X to give Ia/Ib.

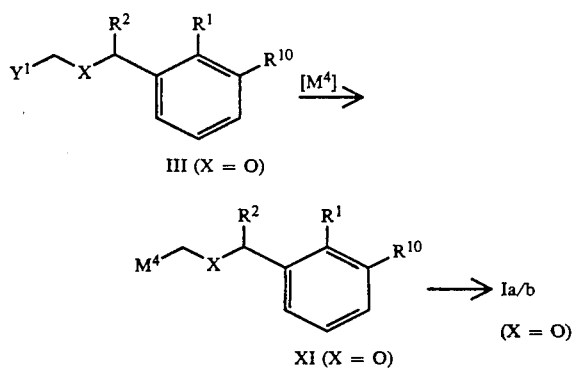

Here, [M⁴] is the metal M⁴ itself or a commercially available alkyl or aryl compound thereof.

The benzyl alcohols XV (X=O, Z²=H) are likewise suitable as starting materials for the preparation of benzyl halides/sulfonates of the type XIII (Y⁵=Cl, Br, I, tosylate or mesylate) by standard methods (cf. Houben-Weyl, Volume 9, pages 388 and 663; Volume 5/3, page 760; Volume 5/4, pages 361 and 610).

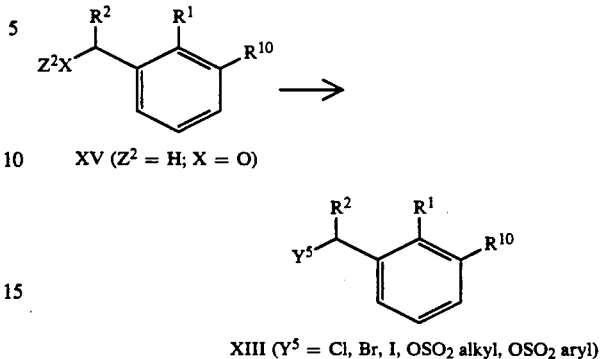

By treating the benzyl alcohols XV (Z=O, Z²=H) with a base (eg. NaH, KH, KO-tert-Bu, NaNH₂), it is possible to produce the corresponding alcoholates XV (X=O, Z=Li, Na, K, Mg or Ca) by conventional methods (cf. Houben-Weyl, Volume 6/2, page 5) and to convert them, either in situ or after purification/isolation, with suitable silanes of the type XIV into the desired products Ia/b (cf. U.S. Pat. No. 2,572,402).

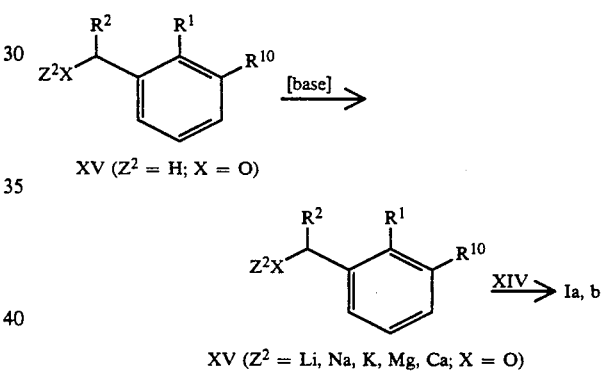

Suitable bases are inorganic compounds, such as alkali metal and alkaline earth metal hydrides, eg. lithium hydride, sodium hydride, potassium hydride and calcium hydride, alkali metal amides, such as lithium amide, sodium amide and potassium amide, organometallic compounds, in particular alkali metal organyls, such as methyllithium, butyllithium and phenyllithium, and alkylmagnesium halides, such as methylmagnesium chloride, or the metals Z² themselves.

Sodium hydride, potassium hydride, sodium amide, methyllithium and butyllithium are particularly preferred.

Benzyl halides of the type XIII are valuable starting materials for the preparation of metal-benzyl compounds by halogen-metal exchange reaction or formal insertion of the metal into the halogen-carbon bond as in the Grignard reaction.

The following reagents are suitable for carrying out the halogen-metal exchange reaction: lithium, sodium, potassium, methyllithium, ethyllithium, n-butyllithium, sec-butyllithium and tert-butyllithium. Halogen-metal exchange reactions are carried out as in Gattermann, Die Praxis des organischen Chemikers, de Gruyter Verlag, Berlin, 43rd Edition, 1982, page 442, and in Houben-Weyl, Volume 13/1, page 134, in inert solvents, such as tetrahydrofuran, or diethyl ether, or at low temperatures (from −120° to 0° C.) under an inert gas (N₂ or Ar).

Grignard compounds (magnesium organyl halides) can be prepared by reaction of a benzyl halide of the type XIII (Y⁵=Cl, Br or I) on magnesium metal in an inert solvent, such as tetrahydrofuran or diethyl ether, under an inert gas (N₂ or Ar) by conventional methods, as described in Gattermann, page 431.

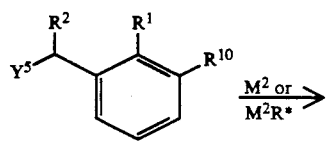

XIII (Y⁵ = Cl, Br, I)

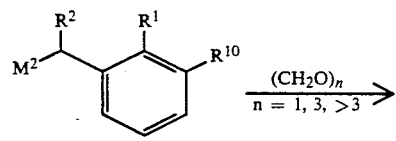

VII (M² = Li, Na, K, ½Mg)

Metal-benzyl compounds of the type VII can be extended by one or two carbon atoms using suitable electrophiles.

For example, reactions with CH₂O, (CH₂O)₃ and (CH₂O)ₙ lead to hydroxymethyl groups, which can be converted in a conventional manner (cf. literature on preparation of compound XIII) into compounds of the type IX (X=CH₂, Y³=Cl, Br, I, ISO₂-alkyl or OSO₂-aryl)

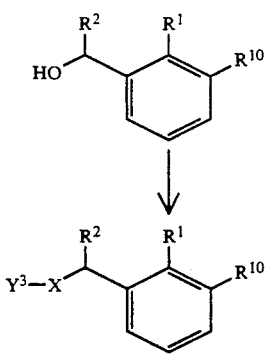

IX (X = CH₂; Y³ = Cl, Br, J, OSO₂ alkyl, OSO₂ aryl)

Reactions of Grignard compounds with formaldehyde or formaldehyde equivalents are described in Houben-Weyl, Volume 13/2, page 290.

Compounds of the type III (X=CH₂) are converted by a method similar to that described above for compounds of the type IX (X=CH₂), by reacting the metal-benzyl compounds VII (M²=Li, Na, K or ½ Mg) with ethylene oxide, into 2-hydroxyethyl derivatives, which in turn can be converted in a conventional manner (cf. literature on preparation of compound XIII) into compounds of the type III.

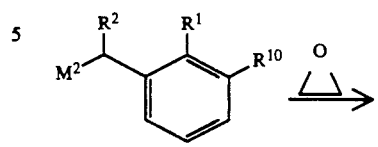

VII (M² = Li, Na, K, ½Mg)

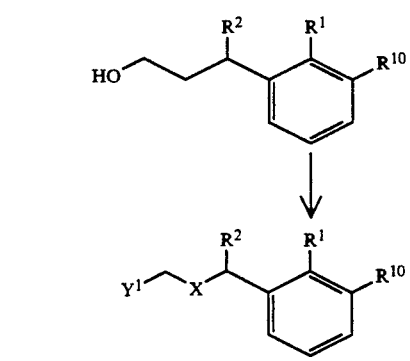

III (X = CH₂; Y¹ = Cl, Br, J, OSO₂ alkyl, OSO₂-aryl)

The examples described in Houben-Weyl, Volume 13/2, page 343 are typical for the reaction of metal organyls with ethylene oxide.

The metal organyls XI (X=CH₂, M⁴=Li, Na, Ka or ½ Mg) can be prepared from compound III (X=CH₂, Y¹=Cl, Br or I) according to the publications already cited above, similarly to the preparation of the compound VII=Li, Na, K or ½ Mg) from the compound XIII (Y⁵=Cl, Br or I).

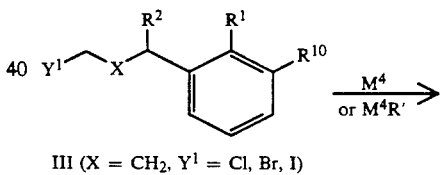

III (X = CH₂, Y¹ = Cl, Br, I)

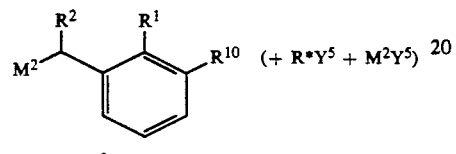

XI (X = CH₂; M⁴ = Li, Na, K, ½Mg)

R] = alkyl, aryl

The preparation of allylbenzene compounds of the type V has been described in many publications, for example:

T. Hirao, Tetrahedron Lett. 27 (1986), 929
A. Luttinghaus, Ann. d. Chem. 557 (1945), 46
Y. Yokoyama, Tetrahedron Lett. 26 (1985), 6457
G. Tolstikov, J. Organomet. Chem. 292 (1985), 133.

Metal-aryl compounds are used as starting materials and are coupled with prop-1-ene compounds nucleofugically substituted in the 3-position, in the presence or absence of one or more catalysts. Suitable catalysts are salts or complexes of metals of groups Ib to VIII of the Periodic Table, for example PdCl₂, Cu(AcAc)₂, or VC₃, where the amount of the catalyst may be from $10^{-3}$ to 1.5 mol equivalents, based on the metal-aryl compound.

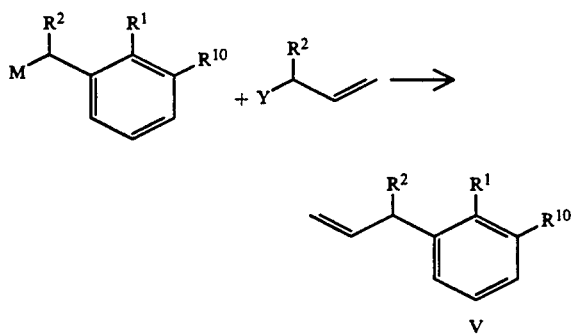

Mg, Li, Na and K are preferred metals and Cl, Br, I, arylsulfonates and alkylsulfonates are preferred nucleofugic groups. The reactions are usually carried out in inert solvents, such as diethyl ether, tetrahydrofuran, pentane, hexane, cyclohexane, heptane, benzene or toluene, at from $-78°$ to $100°$ C. under an inert gas atmosphere ($N_2$ or Ar).

In view of the intended use of the compounds Ia and Ib, suitable substituents are, for example, the following radicals:

R is halogen, such as fluorine, chlorine, bromine or iodine;

alkyl, such as methyl, ethyl, propyl, 1-methylethyl, butyl, 1-methylpropyl, 2-methylpropyl or 1,1-dimethylethyl, preferably methyl or ethyl;

haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl;

alkoxy, such as methoxy, ethoxy, propoxy, 1-methylethoxy, butoxy, 1-methylpropoxy, 2-methylpropoxy or 1,1-dimethylethoxy;

haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy;

alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl;

haloalkenyl, such as 2,2-dichloroethenyl, 2,2-dibromoethenyl, 2,2-difluoroethenyl, 2-chloro-2-fluoroethenyl, 2-bromo-2-chloroethenyl, 2-bromo-2-fluoroethenyl, 2,2-di(trifluoromethyl)-ethenyl, 2-chloro-2-trifluoromethylethenyl or 2-fluoro-2-trifluoromethylethenyl;

phenylethenyl which may carry from one to five halogen atoms, in particular fluorine or chlorine, both on the phenyl ring and on the ethenyl group, in particular 2-chloro-2-(4-chlorophenyl)-ethenyl;

alkynyl, such as ethynyl, 1-propynyl, 2-propynyl, 1-butynyl, 2-butynyl, 3-butynyl or 1-methyl-2-propynyl; cycloalkyl, such as cyclopropyl, cyclobutyl, cyclopentyl, cyclohexyl or cycloheptyl;

aryl, such as phenyl or naphthyl;

hetaryl, such as a 5-membered or 6-membered heteroaromatic system, eg. pyrrolyl, pyrazolyl, imidazolyl, isoxazolyl, oxazolyl, isothiazolyl, thiazolyl, furanyl, thienyl or pyridyl; or a carboxylate group $CO_2R^6$ or a carboxamido group $CONR^7R^8$, where $R^6$, $R^7$ and $R^8$ are each hydrogen, alkyl as stated above or pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, $C_3$–$C_6$-cycloalkyl, such as cyclopropyl, cyclobutyl, cyclopentyl or cyclohexyl, or benzyl, and $R^6$ is preferably methyl or ethyl;

$R^7$ and $R^8$ independently of one another are each hydrogen, $C_1$–$C_6$-alkyl as stated above, $C_3$–$C_6$-cycloalkyl as stated above or benzyl or, together with the nitrogen atom to which they are bonded, form a 3-membered to 8-membered, saturated or monounsaturated or diunsaturated heterocyclic radical consisting of carbon ring members, where this heterocyclic structure may furthermore contain one or two further hetero atoms selected from the group consisting of oxygen, sulfur and nitrogen; examples of preferred ring systems of this type are:

5-membered or 6-membered, saturated or unsaturated heterocyclic structures containing from one to three nitrogen atoms or one or two nitrogen atoms and one oxygen or sulfur atom such as 1-pyrrolidinyl, 1-isoxazolidinyl, 1-isothiazolidinyl, 1-pyrazolidinyl, 1-oxazolidinyl, 1-thiazolidinyl, 1-imidazolidinyl, 1,2,4-oxadiazolidin-1-yl, 1,2,4-thiaoiazolidin-1-yl, 1,2,4-triazolidin-1-yl, 1,3,4-oxadiazolidin-1-yl, 1,3,4-thiadiazolidin-1-yl, 1,3,4-oxadiazolidin-1-yl, 1,3,4-thiadiazolidin-1-yl, 1,3,4-triazolidin-1-yl, 2,3-pyrrolin-1-yl, 2,4-pyrrolin-1-yl, 2,3-isoxazolin-1-yl, 3,4-isoxazolin-1-yl, 4,5-isoxazolin-1-yl, 2,3-isothiazolin-1-yl, 3,4-isothiazolin-1-yl, 4,5-isothiazolin-1-yl, 2,3-dihydropyrazol-1-yl, 3,4-dihydropyrazol-1-yl, 4,5-dihydropyrazol-1-yl, 2,3-dihydrooxazol-1-yl, 3,4-dihydrooxazol-1-yl, 3,4-dihydrooxazol-1-yl, 1-imidazolyl, 1,2,4-oxadiazol-1-yl, 1,2,4-thiadiazol-1-yl, 1,2,4-triazol-1-yl, 1,3,4-oxadiazol-1-yl, 1,3,4-thiadiazol-1-yl or 1,3,4-triazol-1-yl, 1-piperidinyl, 1-tetrahydropyridazinyl, 1-tetrahydropyrimidinyl, 1-tetrahydropyrazinyl, 1,3,5-tetrahydrotriazin-1-yl or 1,2,4-tetrahydrotriazin-1-yl, 1-pyrrolyl, 1-isoxazolyl, 1-isothiazolyl, 1-pyrazolyl, 1-oxazolyl, 1-thiazolyl, 1-imidazolyl or 1,2,4-oxadiazol-1-yl, 1,2,4-thiadiazol-1-yl, 1,2,4-triazol-1-yl, 1,3,4-oxadiazol-1-yl, 1,3,4-thiadiazol-1-yl or 1,3,4-triazol-1-yl;

$R^7$ and $R^8$ are each preferably methyl or ethyl;

n is 0, 1 or 2, and the radicals R may be different when n is 2;

$R^1$ is halogen as stated for R, preferably fluorine or chlorine, or alkyl as stated for $R^7$, preferably methyl or ethyl;

$R^2$ is hydrogen;

alkyl as stated for R;

alkenyl as stated for R;

alkynyl as stated for R, preferably ethynyl; or cyano;

$R^3$ and $R^4$ independently of one another are each $C_1$–$C_4$-alkyl, preferably methyl, ethyl or propyl, in particular methyl, or $C_2$–$C_8$-alkenyl, preferably Cz-C:-alkenyl, such as ethenyl, 1-propenyl, 2-propenyl, 1-methylethenyl, 1- butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl;

where these radicals may carry from one to nine halogen atoms, such as fluorine, chlorine, bromine or iodine, preferably fluorine or chlorine, in particular fluorine, and/or one of the following groups:

$C_3$–$C_8$-cycloalkyl, such as cyclopropyl, cyclobutyl, cyclopentyl, cyclohexyl, cycloheptyl or cyclooctyl, in particular cyclopropyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular trifluoromethoxy;

$C_1$–$C_4$-alkylthio, such as methylthio, ethylthio, propylthio, 1-methylethylthio, butylthio, 1-methylpropylthio, 2-methylpropylthio, 1,1-dimethylethylthio, in particular methylthio;

$C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, in particular trifluoroethylthio;

phenyl, phenoxy and phenylthio, where the aromatic groups in turn may carry from one to five halogen atoms, such as fluorine, chlorine, bromine or iodine, preferably fluorine or chlorine, and/or from one to three of the following groups:

$C_1$–$C_4$-alkyl, such as methyl, ethyl, propyl, 1-methylethyl, butyl, 1-methylpropyl, 2-methylpropyl or 1,1-dimethylethyl, preferably methyl, ethyl or propyl;

$C_1$–$C_4$-haloalkyl, in particular $C_1$-or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or propoxy, in particular methoxy or ethoxy;

$C_1$–$C_4$-haloalkoxy, in particular $C_2$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably trifluoromethoxy or pentafluoroethoxy;

$C_1$–$C_4$-alkylthio, such as methylthio, ethylthio, propylthio, 1-methylethylthio, butylthio, 1-methylpropylthio, 2-methylpropylthio, 1,1-dimethylethylthio, preferably methylthio or ethylthio;

or $C_1$–$C_1$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trifluoromethylthio or pentafluoroethylthio;

$C_3$–$C_8$-cycloalkyl as stated above in general and in particular, which may carry from one to three of the following groups: halogen, such as fluorine, chlorine, bromine or iodine, preferably fluorine or chlorine;

$C_1$–$C_4$-alkyl, such as methyl, ethyl, propyl, 1-methylethyl, butyl, 1-methylpropyl, 2-methylpropyl or 1,1-dimethylethyl, in particular methyl;

$C_1$–$C_1$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy or ethoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2- difluoroethoxy, 2,2-dichloro-2-fluoroethoxy, 2,2,2-trichloroethoxy or pentafluoroethoxy, in particular trifluoromethoxy;

$C_1$-$C_4$-alkylthio, such as methylthio, ethylthio, propylthio, 1-methylethylthio, butylthio, 1-methylpropylthio, 2-methylpropylthio, 1,1-dimethylethylthio, in particular methylthio or ethylthio;

or $C_1$-$C_1$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, in particular trifluoromethylthio;

phenyl, naphthyl, pyridyl or pyrimidyl, where the aromatic radicals may carry from one to seven halogen atoms, such as fluorine, chlorine, bromine or iodine, preferably fluorine or chlorine, in particular fluorine, and/or from one to four of the following groups:

$C_1$-$C_4$-alkyl, such as methyl, ethyl, propyl, 1-methylethyl, butyl, 1-methylpropyl, 2-methylpropyl or 1,1-dimethylethyl, preferably methyl, ethyl or propyl, in particular methyl;

$C_1$-$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trifluoromethyl or pentafluoroethyl, in particular trifluoromethyl;

$C_1$-$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or propoxy, in particular ethoxy;

$C_1$-$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular trifluoromethoxy;

$C_1$-$C_4$-alkylthio, such as methylthio, ethylthio, propylthio, 1-methylethylthio, butylthio, 1-methylpropylthio, 2-methylpropylthio or 1,1-dimethylethylthio, in particular ethylthio;

or $C_1$-$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, in particular trifluoromethylthio;

or $R^3$ and $R^4$ together form $C_2$-$C_5$-alkylene, such as ethylene (—$CH_2CH_2$—), propylene (—$CH_2CH_2CH_2$—), butylene (—$CH_2CH_2CH_2CH_2$—) or pentylene (—$CH_2CH_2CH_2CH_2CH_2$—), which may carry from one to three $C_1$-$C_3$-alkyl groups, such as methyl, ethyl, propyl or 1-methylethyl, preferably butylene or pentylene;

$R^5$ is hydrogen;

$C_5$-$C_{18}$-alkyl, in particular $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

where this radical may carry from one to nine halogen atoms, such as fluorine, chlorine, bromine or iodine, preferably fluorine or chlorine, in particular fluorine, and/or one of the following groups:

$C_3$-$C_8$-cycloalkyl, such as cyclopropyl, cyclobutyl, cyclopentyl, cyclohexyl, cycloheptyl or cyclooctyl, in particular cyclopropyl;

$C_1$-$C_4$-alkoxy, such as methoxy, ethoxy, propoxy, 1-methylethoxy, butoxy, 1-methylpropoxy, 2-methylpropoxy or 1,1-dimethylethoxy, in particular methoxy;

$C_1$-$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular trifluoromethoxy;

$C_1$-$C_4$-alkylthio, such as methylthio, ethylthio, propylthio, 1-methylethylthio, butylthio, 1-methylpropylthio, 2-methylpropylthio, 1,1-dimethylethylthio, in particular methylthio;

$C_1$-$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, in particular trifluoromethylthio;

phenyl, phenoxy or phenylthio, where the aromatic groups in turn may carry from one to five halogen atoms, such as fluorine, chlorine, bromine or iodine, preferably fluorine or chlorine, and/or from one to three of the following groups:

$C_1$-$C_4$-alkyl, such as methyl, ethyl, propyl, 1-methylethyl, butyl, 1-methylpropyl, 2-methylpropyl or 1,1-dimethylethyl, preferably methyl, ethyl or propyl;

$C_1$-$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$-$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or propoxy, in particular methoxy or ethoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably trifluoromethoxy or pentafluoroethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, preferably methylthio or ethylthio;

or $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trifluoroethylthio or pentafluoroethylthio;

or one of the groups stated in general and in particular for $R^3$;

X is $CH_2$, O, S, NH or $NR^9$, where $R^9$ is $C_1$–$C_4$-alkyl, such as methyl, ethyl, propyl, 1-methylethyl, butyl, 1-methylpropyl, 2-methylpropyl or 1,1-dimethylethyl, preferably methyl or ethyl, in particular methyl;

$C_3$–$C_6$-cycloalkyl, such as cyclopropyl, cyclobutyl, cyclopentyl or cyclohexyl, in particular cyclopropyl;

$C_2$–$C_4$-alkenyl, such as ethenyl, 2-propenyl, 2-butenyl or 3-butenyl, in particular 2-propenyl;

$C_2$–$C_4$-alkynyl, such as ethynyl, 2-propynyl, 2-butynyl or 3-butynyl, in particular 2-propynyl;

or benzyl which in turn may carry from one to five halogen atoms, such as fluorine, chlorine, bromine or iodine, preferably fluorine or chlorine, and/or from one to three of the following groups:

$C_1$–$C_4$-alkyl, such as methyl, ethyl, propyl, 1-methylethyl, butyl, 1-methylpropyl, 2-methylpropyl or 1,1-dimethylethyl, in particular methyl;

$C_1$–$C.$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy or ethoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular trifluoromethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular ethylthio;

or $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, in particular trifluoromethylthio.

3-Isoxazolylphenyl compounds of the general formulae Ia and Ib in which R is methyl or ethyl and $R^2$ is hydrogen are preferred for pest control in view of their biological activity.

Other preferred 3-isoxazolylphenyl compounds of the general formulae Ia and Ib are those in which $R^1$ is methyl or ethyl, $R^2$ is hydrogen and n is 0.

The 3-isoxazolylphenyl compounds of the general formulae Ia and Ib in which $R^5$ is hydrogen or methyl and $R^4$ is methyl or cyclopropyl are also preferred.

Further preferred 3-isoxazolylphenyl compounds of the general formulae Ia and Ib are those in which $R^3$ is phenyl, pyridyl or pyrimidinyl, where the aromatic radicals may carry from one to five halogen atoms and the following groups stated in general and in particular above: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio.

Furthermore, particularly preferred 3-isoxazolylphenyl compounds of the general formulae Ia and Ib are those in which $R^5$ is hydrogen or methyl, $R^4$ is methyl or cyclopropyl and $R^3$ is phenyl, pyridyl or pyrimidinyl, where the aromatic radicals may carry from one to five halogen atoms as stated above in general and in particular and/or from one to three of the following groups stated above in general and in particular: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio.

Examples of particularly active compounds Ia and Ib are shown in the table below. The combinations of substituents given in each line of the table relate to each of formulae Ia.1, Ia.2, Ib.1 and Ib.2:

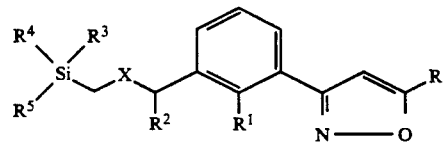

Ia.1 (n = 1; $R^5$ = 4-$R^a$-phenyl, $R^3$ = $R^4$ = $CH_3$)

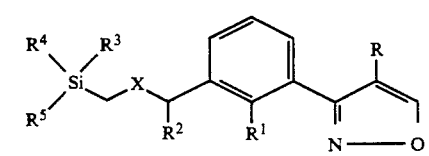

Ia.2 (n = 1; $R^5$ = 4-$R^a$-phenyl, $R^3$ = $R^4$ = $CH_3$)

-continued

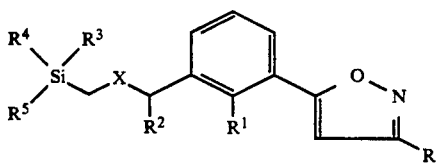

Ib.1 (n = 1; $R^5$ = 4-$R^a$-phenyl, $R^3$ = $R^4$ = $CH_3$)

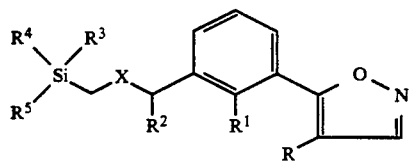

Ib.2 (n = 1; $R^5$ = 4-$R^a$-phenyl, $R^3$ = $R^4$ = $CH_3$)

TABLE

| R | $R^1$ | $R^2$ | $R^a$ | X |
|---|---|---|---|---|
| H | $CH_3$ | H | H | O |
| $C_6H_5$ | $CH_3$ | H | H | O |
| $CH_3$ | $CH_3$ | H | H | O |
| $C_2H_5$ | $CH_3$ | H | H | O |
| H | Cl | H | H | O |
| $C_6H_5$ | Cl | H | H | O |
| $CH_3$ | Cl | H | H | O |
| $C_2H_5$ | Cl | H | H | O |
| H | H | H | H | O |
| $C_6H_5$ | H | H | H | O |
| $CH_3$ | H | H | H | O |
| $C_2H_5$ | H | H | H | O |
| H | $CH_3$ | CN | H | O |
| $C_6H_5$ | $CH_3$ | CN | H | O |
| $CH_3$ | $CH_3$ | CN | H | O |
| $C_2H_5$ | $CH_3$ | CN | H | O |
| H | Cl | CN | H | O |
| $C_6H_5$ | Cl | CN | H | O |
| $CH_3$ | Cl | CN | H | O |
| $C_2H_5$ | Cl | CN | H | O |
| H | H | CN | H | O |
| $C_6H_5$ | H | CN | H | O |
| $CH_3$ | H | CN | H | O |
| $C_2H_5$ | H | CN | H | O |
| H | $CH_3$ | C≡CH | H | O |
| $C_6H_5$ | $CH_3$ | C≡CH | H | O |
| $CH_3$ | $CH_3$ | C≡CH | H | O |
| $C_2H_5$ | $CH_3$ | C≡CH | H | O |
| H | Cl | C≡CH | H | O |
| $C_6H_5$ | Cl | C≡CH | H | O |
| $CH_3$ | Cl | C≡CH | H | O |
| $C_2H_5$ | Cl | C≡CH | H | O |
| H | H | C≡CH | H | O |
| $C_6H_5$ | H | C≡CH | H | O |
| $CH_3$ | H | C≡CH | H | O |
| $C_2H_5$ | H | C≡CH | H | O |
| H | $CH_3$ | H | $CH_3$ | O |
| $C_6H_5$ | $CH_3$ | H | $CH_3$ | O |
| $CH_3$ | $CH_3$ | H | $CH_3$ | O |
| $C_2H_5$ | $CH_3$ | H | $CH_3$ | O |
| H | Cl | H | $CH_3$ | O |
| $C_6H_5$ | Cl | H | $CH_3$ | O |
| $CH_3$ | Cl | H | $CH_3$ | O |
| $C_2H_5$ | Cl | H | $CH_3$ | O |
| H | H | H | $CH_3$ | O |
| $C_6H_5$ | H | H | $CH_3$ | O |
| $CH_3$ | H | H | $CH_3$ | O |
| $C_2H_5$ | H | H | $CH_3$ | O |
| H | $CH_3$ | CN | $CH_3$ | O |
| $C_6H_5$ | $CH_3$ | CN | $CH_3$ | O |
| $CH_3$ | $CH_3$ | CN | $CH_3$ | O |
| $C_2H_5$ | $CH_3$ | CN | $CH_3$ | O |
| H | Cl | CN | $CH_3$ | O |
| $C_6H_5$ | Cl | CN | $CH_3$ | O |
| $CH_3$ | Cl | CN | $CH_3$ | O |
| $C_2H_5$ | Cl | CN | $CH_3$ | O |
| H | H | CN | $CH_3$ | O |
| $C_6H_5$ | H | CN | $CH_3$ | O |
| $CH_3$ | H | CN | $CH_3$ | O |
| $C_2H_5$ | H | CN | $CH_3$ | O |
| H | $CH_3$ | C≡CH | $CH_3$ | O |
| $C_6H_5$ | $CH_3$ | C≡CH | $CH_3$ | O |
| $CH_3$ | $CH_3$ | C≡CH | $CH_3$ | O |
| $C_2H_5$ | $CH_3$ | C≡CH | $CH_3$ | O |
| H | Cl | C≡CH | $CH_3$ | O |
| $C_6H_5$ | Cl | C≡CH | $CH_3$ | O |
| $CH_3$ | Cl | C≡CH | $CH_3$ | O |
| $C_2H_5$ | Cl | C≡CH | $CH_3$ | O |
| H | H | C≡CH | $CH_3$ | O |
| $C_6H_5$ | H | C≡CH | $CH_3$ | O |
| $CH_3$ | H | C≡CH | $CH_3$ | O |
| $C_2H_5$ | H | C≡CH | $CH_3$ | O |
| H | $CH_3$ | H | $OCH_3$ | O |
| $C_6H_5$ | $CH_3$ | H | $OCH_3$ | O |
| $CH_3$ | $CH_3$ | H | $OCH_3$ | O |
| $C_2H_5$ | $CH_3$ | H | $OCH_3$ | O |
| H | Cl | H | $OCH_3$ | O |
| $C_6H_5$ | Cl | H | $OCH_3$ | O |
| $CH_3$ | Cl | H | $OCH_3$ | O |
| $C_2H_5$ | Cl | H | $OCH_3$ | O |
| H | H | H | $OCH_3$ | O |
| $C_6H_5$ | H | H | $OCH_3$ | O |
| $CH_3$ | H | H | $OCH_3$ | O |
| $C_2H_5$ | H | H | $OCH_3$ | O |
| H | $CH_3$ | CN | $OCH_3$ | O |
| $C_6H_5$ | $CH_3$ | CN | $OCH_3$ | O |
| $CH_3$ | $CH_3$ | CN | $OCH_3$ | O |
| $C_2H_5$ | $CH_3$ | CN | $OCH_3$ | O |
| H | Cl | CN | $OCH_3$ | O |
| $C_6H_5$ | Cl | CN | $OCH_3$ | O |
| $CH_3$ | Cl | CN | $OCH_3$ | O |
| $C_2H_5$ | Cl | CN | $OCH_3$ | O |
| H | H | CN | $OCH_3$ | O |
| $C_6H_5$ | H | CN | $OCH_3$ | O |
| $CH_3$ | H | CN | $OCH_3$ | O |
| $C_2H_5$ | H | CN | $OCH_3$ | O |
| H | $CH_3$ | C≡CH | $OCH_3$ | O |
| $C_6H_5$ | $CH_3$ | C≡CH | $OCH_3$ | O |
| $CH_3$ | $CH_3$ | C≡CH | $OCH_3$ | O |
| $C_2H_5$ | $CH_3$ | C≡CH | $OCH_3$ | O |
| H | Cl | C≡CH | $OCH_3$ | O |
| $C_6H_5$ | Cl | C≡CH | $OCH_3$ | O |
| $CH_3$ | Cl | C≡CH | $OCH_3$ | O |
| $C_2H_5$ | Cl | C≡CH | $OCH_3$ | O |
| H | H | C≡CH | $OCH_3$ | O |
| $C_6H_5$ | H | C≡CH | $OCH_3$ | O |
| $CH_3$ | H | C≡CH | $OCH_3$ | O |
| $C_2H_5$ | H | C≡CH | $OCH_3$ | O |
| H | $CH_3$ | H | $C_2H_5$ | O |
| $C_6H_5$ | $CH_3$ | H | $C_2H_5$ | O |
| $CH_3$ | $CH_3$ | H | $C_2H_5$ | O |
| $C_2H_5$ | $CH_3$ | H | $C_2H_5$ | O |
| H | Cl | H | $C_2H_5$ | O |
| $C_6H_5$ | Cl | H | $C_2H_5$ | O |
| $CH_3$ | Cl | H | $C_2H_5$ | O |
| $C_2H_5$ | Cl | H | $C_2H_5$ | O |
| H | H | H | $C_2H_5$ | O |
| $C_6H_5$ | H | H | $C_2H_5$ | O |
| $CH_3$ | H | H | $C_2H_5$ | O |
| $C_2H_5$ | H | H | $C_2H_5$ | O |
| H | $CH_3$ | CN | $C_2H_5$ | O |
| $C_6H_5$ | $CH_3$ | CN | $C_2H_5$ | O |
| $CH_3$ | $CH_3$ | CN | $C_2H_5$ | O |
| $C_2H_5$ | $CH_3$ | CN | $C_2H_5$ | O |
| H | Cl | CN | $C_2H_5$ | O |
| $C_6H_5$ | Cl | CN | $C_2H_5$ | O |
| $CH_3$ | Cl | CN | $C_2H_5$ | O |
| $C_2H_5$ | Cl | CN | $C_2H_5$ | O |
| H | H | CN | $C_2H_5$ | O |
| $C_6H_5$ | H | CN | $C_2H_5$ | O |
| $CH_3$ | H | CN | $C_2H_5$ | O |
| $C_2H_5$ | H | CN | $C_2H_5$ | O |
| H | $CH_3$ | C≡CH | $C_2H_5$ | O |
| $C_6H_5$ | $CH_3$ | C≡CH | $C_2H_5$ | O |
| $CH_3$ | $CH_3$ | C≡CH | $C_2H_5$ | O |
| $C_2H_5$ | $CH_3$ | C≡CH | $C_2H_5$ | O |
| H | Cl | C≡CH | $C_2H_5$ | O |
| $C_6H_5$ | Cl | C≡CH | $C_2H_5$ | O |
| $CH_3$ | Cl | C≡CH | $C_2H_5$ | O |

TABLE-continued

| R | R¹ | R² | Rᵃ | X |
|---|---|---|---|---|
| C₂H₅ | Cl | C≡CH | C₂H₅ | O |
| H | H | C≡CH | C₂H₅ | O |
| C₆H₅ | H | C≡CH | C₂H₅ | O |
| CH₃ | H | C≡CH | C₂H₅ | O |
| C₂H₅ | H | C≡CH | C₂H₅ | O |
| H | CH₃ | H | OC₂H₅ | O |
| C₆H₅ | CH₃ | H | OC₂H₅ | O |
| CH₃ | CH₃ | H | OC₂H₅ | O |
| C₂H₅ | CH₃ | H | OC₂H₅ | O |
| H | Cl | H | OC₂H₅ | O |
| C₆H₅ | Cl | H | OC₂H₅ | O |
| CH₃ | Cl | H | OC₂H₅ | O |
| C₂H₅ | Cl | H | OC₂H₅ | O |
| H | H | H | OC₂H₅ | O |
| C₆H₅ | H | H | OC₂H₅ | O |
| CH₃ | H | H | OC₂H₅ | O |
| C₂H₅ | H | H | OC₂H₅ | O |
| H | CH₃ | CN | OC₂H₅ | O |
| C₆H₅ | CH₃ | CN | OC₂H₅ | O |
| CH₃ | CH₃ | CN | OC₂H₅ | O |
| C₂H₅ | CH₃ | CN | OC₂H₅ | O |
| H | Cl | CN | OC₂H₅ | O |
| C₆H₅ | Cl | CN | OC₂H₅ | O |
| CH₃ | Cl | CN | OC₂H₅ | O |
| C₂H₅ | Cl | CN | OC₂H₅ | O |
| H | H | CN | OC₂H₅ | O |
| C₆H₅ | H | CN | OC₂H₅ | O |
| CH₃ | H | CN | OC₂H₅ | O |
| C₂H₅ | H | CN | OC₂H₅ | O |
| H | CH₃ | C≡CH | OC₂H₅ | O |
| C₆H₅ | CH₃ | C≡CH | OC₂H₅ | O |
| CH₃ | CH₃ | C≡CH | OC₂H₅ | O |
| C₂H₅ | CH₃ | C≡CH | OC₂H₅ | O |
| H | Cl | C≡CH | OC₂H₅ | O |
| C₆H₅ | Cl | C≡CH | OC₂H₅ | O |
| CH₃ | Cl | C≡CH | OC₂H₅ | O |
| C₂H₅ | Cl | C≡CH | OC₂H₅ | O |
| H | H | C≡CH | OC₂H₅ | O |
| C₆H₅ | H | C≡CH | OC₂H₅ | O |
| CH₃ | H | C≡CH | OC₂H₅ | O |
| C₂H₅ | H | C≡CH | OC₂H₅ | O |
| H | CH₃ | H | CF₃ | O |
| C₆H₅ | CH₃ | H | CF₃ | O |
| CH₃ | CH₃ | H | CF₃ | O |
| C₂H₅ | CH₃ | H | CF₃ | O |
| H | Cl | H | CF₃ | O |
| C₆H₅ | Cl | H | CF₃ | O |
| CH₃ | Cl | H | CF₃ | O |
| C₂H₅ | Cl | H | CF₃ | O |
| H | H | H | CF₃ | O |
| C₆H₅ | H | H | CF₃ | O |
| CH₃ | H | H | CF₃ | O |
| C₂H₅ | H | H | CF₃ | O |
| H | CH₃ | CN | CF₃ | O |
| C₆H₅ | CH₃ | CN | CF₃ | O |
| CH₃ | CH₃ | CN | CF₃ | O |
| C₂H₅ | CH₃ | CN | CF₃ | O |
| H | Cl | CN | CF₃ | O |
| C₆H₅ | Cl | CN | CF₃ | O |
| CH₃ | Cl | CN | CF₃ | O |
| C₂H₅ | Cl | CN | CF₃ | O |
| H | H | CN | CF₃ | O |
| C₆H₅ | H | CN | CF₃ | O |
| CH₃ | H | CN | CF₃ | O |
| C₂H₅ | H | CN | CF₃ | O |
| H | CH₃ | C≡CH | CF₃ | O |
| C₆H₅ | CH₃ | C≡CH | CF₃ | O |
| CH₃ | CH₃ | C≡CH | CF₃ | O |
| C₂H₅ | CH₃ | C≡CH | CF₃ | O |
| H | Cl | C≡CH | CF₃ | O |
| C₆H₅ | Cl | C≡CH | CF₃ | O |
| CH₃ | Cl | C≡CH | CF₃ | O |
| C₂H₅ | Cl | C≡CH | CF₃ | O |
| H | H | C≡CH | CF₃ | O |
| C₆H₅ | H | C≡CH | CF₃ | O |
| CH₃ | H | C≡CH | CF₃ | O |
| C₂H₅ | H | C≡CH | CF₃ | O |
| H | CH₃ | H | F | O |
| C₆H₅ | CH₃ | H | F | O |
| CH₃ | CH₃ | H | F | O |
| C₂H₅ | CH₃ | H | F | O |
| H | Cl | H | F | O |
| C₆H₅ | Cl | H | F | O |
| CH₃ | Cl | H | F | O |
| C₂H₅ | Cl | H | F | O |
| H | H | H | F | O |
| C₆H₅ | H | H | F | O |
| CH₃ | H | H | F | O |
| C₂H₅ | H | H | F | O |
| H | CH₃ | CN | F | O |
| C₆H₅ | CH₃ | CN | F | O |
| CH₃ | CH₃ | CN | F | O |
| C₂H₅ | CH₃ | CN | F | O |
| H | Cl | CN | F | O |
| C₆H₅ | Cl | CN | F | O |
| CH₃ | Cl | CN | F | O |
| C₂H₅ | Cl | CN | F | O |
| H | H | CN | F | O |
| C₆H₅ | H | CN | F | O |
| CH₃ | H | CN | F | O |
| C₂H₅ | H | CN | F | O |
| H | CH₃ | C≡CH | F | O |
| C₆H₅ | CH₃ | C≡CH | F | O |
| CH₃ | CH₃ | C≡CH | F | O |
| C₂H₅ | CH₃ | C≡CH | F | O |
| H | Cl | C≡CH | F | O |
| C₆H₅ | Cl | C≡CH | F | O |
| CH₃ | Cl | C≡CH | F | O |
| C₂H₅ | Cl | C≡CH | F | O |
| H | H | C≡CH | F | O |
| C₆H₅ | H | C≡CH | F | O |
| CH₃ | H | C≡CH | F | O |
| C₂H₅ | H | C≡CH | F | O |
| H | CH₃ | H | Cl | O |
| C₆H₅ | CH₃ | H | Cl | O |
| CH₃ | CH₃ | H | Cl | O |
| C₂H₅ | CH₃ | H | Cl | O |
| H | Cl | H | Cl | O |
| C₆H₅ | Cl | H | Cl | O |
| CH₃ | Cl | H | Cl | O |
| C₂H₅ | Cl | H | Cl | O |
| H | H | H | Cl | O |
| C₆H₅ | H | H | Cl | O |
| CH₃ | H | H | Cl | O |
| C₂H₅ | H | H | Cl | O |
| H | CH₃ | CN | Cl | O |
| C₆H₅ | CH₃ | CN | Cl | O |
| CH₃ | CH₃ | CN | Cl | O |
| C₂H₅ | CH₃ | CN | Cl | O |
| H | Cl | CN | Cl | O |
| C₆H₅ | Cl | CN | Cl | O |
| CH₃ | Cl | CN | Cl | O |
| C₂H₅ | Cl | CN | Cl | O |
| H | H | CN | Cl | O |
| C₆H₅ | H | CN | Cl | O |
| CH₃ | H | CN | Cl | O |
| C₂H₅ | H | CN | Cl | O |
| H | CH₃ | C≡CH | Cl | O |
| C₆H₅ | CH₃ | C≡CH | Cl | O |
| CH₃ | CH₃ | C≡CH | Cl | O |
| C₂H₅ | CH₃ | C≡CH | Cl | O |
| H | Cl | C≡CH | Cl | O |
| C₆H₅ | Cl | C≡CH | Cl | O |
| CH₃ | Cl | C≡CH | Cl | O |
| C₂H₅ | Cl | C≡CH | Cl | O |
| H | H | C≡CH | Cl | O |
| C₆H₅ | H | C≡CH | Cl | O |
| CH₃ | H | C≡CH | Cl | O |
| C₂H₅ | H | C≡CH | Cl | O |
| H | CH₃ | H | H | S |
| C₆H₅ | CH₃ | H | H | S |
| CH₃ | CH₃ | H | H | S |
| C₂H₅ | CH₃ | H | H | S |
| H | Cl | H | H | S |
| C₆H₅ | Cl | H | H | S |
| CH₃ | Cl | H | H | S |
| C₂H₅ | Cl | H | H | S |
| H | H | H | H | S |
| C₆H₅ | H | H | H | S |
| CH₃ | H | H | H | S |
| C₂H₅ | H | H | H | S |
| H | CH₃ | CN | H | S |

TABLE-continued

| R | R¹ | R² | Rᵃ | X |
|---|---|---|---|---|
| C₆H₅ | CH₃ | CN | H | S |
| CH₃ | CH₃ | CN | H | S |
| C₂H₅ | CH₃ | CN | H | S |
| H | Cl | CN | H | S |
| C₆H₅ | Cl | CN | H | S |
| CH₃ | Cl | CN | H | S |
| C₂H₅ | Cl | CN | H | S |
| H | H | CN | H | S |
| C₆H₅ | H | CN | H | S |
| CH₃ | H | CN | H | S |
| C₂H₅ | H | CN | H | S |
| H | CH₃ | C≡CH | H | S |
| C₆H₅ | CH₃ | C≡CH | H | S |
| CH₃ | CH₃ | C≡CH | H | S |
| C₂H₅ | CH₃ | C≡CH | H | S |
| H | Cl | C≡CH | H | S |
| C₆H₅ | Cl | C≡CH | H | S |
| CH₃ | Cl | C≡CH | H | S |
| C₂H₅ | Cl | C≡CH | H | S |
| H | H | C≡CH | H | S |
| C₆H₅ | H | C≡CH | H | S |
| CH₃ | H | C≡CH | H | S |
| C₂H₅ | H | C≡CH | H | S |
| H | CH₃ | H | CH₃ | S |
| C₆H₅ | CH₃ | H | CH₃ | S |
| CH₃ | CH₃ | H | CH₃ | S |
| C₂H₅ | CH₃ | H | CH₃ | S |
| H | Cl | H | CH₃ | S |
| C₆H₅ | Cl | H | CH₃ | S |
| CH₃ | Cl | H | CH₃ | S |
| C₂H₅ | Cl | H | CH₃ | S |
| H | H | H | CH₃ | S |
| C₆H₅ | H | H | CH₃ | S |
| CH₃ | H | H | CH₃ | S |
| C₂H₅ | H | H | CH₃ | S |
| H | CH₃ | CN | CH₃ | S |
| C₆H₅ | CH₃ | CN | CH₃ | S |
| CH₃ | CH₃ | CN | CH₃ | S |
| C₂H₅ | CH₃ | CN | CH₃ | S |
| H | Cl | CN | CH₃ | S |
| C₆H₅ | Cl | CN | CH₃ | S |
| CH₃ | Cl | CN | CH₃ | S |
| C₂H₅ | Cl | CN | CH₃ | S |
| H | H | CN | CH₃ | S |
| C₆H₅ | H | CN | CH₃ | S |
| CH₃ | H | CN | CH₃ | S |
| C₂H₅ | H | CN | CH₃ | S |
| H | CH₃ | C≡CH | CH₃ | S |
| C₆H₅ | CH₃ | C≡CH | CH₃ | S |
| CH₃ | CH₃ | C≡CH | CH₃ | S |
| C₂H₅ | CH₃ | C≡CH | CH₃ | S |
| H | Cl | C≡CH | CH₃ | S |
| C₆H₅ | Cl | C≡CH | CH₃ | S |
| CH₃ | Cl | C≡CH | CH₃ | S |
| C₂H₅ | Cl | C≡CH | CH₃ | S |
| H | H | C≡CH | CH₃ | S |
| C₆H₅ | H | C≡CH | CH₃ | S |
| CH₃ | H | C≡CH | CH₃ | S |
| C₂H₅ | H | C≡CH | CH₃ | S |
| H | CH₃ | H | OCH₃ | S |
| C₆H₅ | CH₃ | H | OCH₃ | S |
| CH₃ | CH₃ | H | OCH₃ | S |
| C₂H₅ | CH₃ | H | OCH₃ | S |
| H | Cl | H | OCH₃ | S |
| C₆H₅ | Cl | H | OCH₃ | S |
| CH₃ | Cl | H | OCH₃ | S |
| C₂H₅ | Cl | H | OCH₃ | S |
| H | H | H | OCH₃ | S |
| C₆H₅ | H | H | OCH₃ | S |
| CH₃ | H | H | OCH₃ | S |
| C₂H₅ | H | H | OCH₃ | S |
| H | CH₃ | CN | OCH₃ | S |
| C₆H₅ | CH₃ | CN | OCH₃ | S |
| CH₃ | CH₃ | CN | OCH₃ | S |
| C₂H₅ | CH₃ | CN | OCH₃ | S |
| H | Cl | CN | OCH₃ | S |
| C₆H₅ | Cl | CN | OCH₃ | S |
| CH₃ | Cl | CN | OCH₃ | S |
| C₂H₅ | Cl | CN | OCH₃ | S |
| H | H | CN | OCH₃ | S |
| C₆H₅ | H | CN | OCH₃ | S |
| CH₃ | H | CN | OCH₃ | S |
| C₂H₅ | H | CN | OCH₃ | S |
| H | CH₃ | C≡CH | OCH₃ | S |
| C₆H₅ | CH₃ | C≡CH | OCH₃ | S |
| CH₃ | CH₃ | C≡CH | OCH₃ | S |
| C₂H₅ | CH₃ | C≡CH | OCH₃ | S |
| H | Cl | C≡CH | OCH₃ | S |
| C₆H₅ | Cl | C≡CH | OCH₃ | S |
| CH₃ | Cl | C≡CH | OCH₃ | S |
| C₂H₅ | Cl | C≡CH | OCH₃ | S |
| H | H | C≡CH | OCH₃ | S |
| C₆H₅ | H | C≡CH | OCH₃ | S |
| CH₃ | H | C≡CH | OCH₃ | S |
| C₂H₅ | H | C≡CH | OCH₃ | S |
| H | CH₃ | H | C₂H₅ | S |
| C₆H₅ | CH₃ | H | C₂H₅ | S |
| CH₃ | CH₃ | H | C₂H₅ | S |
| C₂H₅ | CH₃ | H | C₂H₅ | S |
| H | Cl | H | C₂H₅ | S |
| C₆H₅ | Cl | H | C₂H₅ | S |
| CH₃ | Cl | H | C₂H₅ | S |
| C₂H₅ | Cl | H | C₂H₅ | S |
| H | H | H | C₂H₅ | S |
| C₆H₅ | H | H | C₂H₅ | S |
| CH₃ | H | H | C₂H₅ | S |
| C₂H₅ | H | H | C₂H₅ | S |
| H | CH₃ | CN | C₂H₅ | S |
| C₆H₅ | CH₃ | CN | C₂H₅ | S |
| CH₃ | CH₃ | CN | C₂H₅ | S |
| C₂H₅ | CH₃ | CN | C₂H₅ | S |
| H | Cl | CN | C₂H₅ | S |
| C₆H₅ | Cl | CN | C₂H₅ | S |
| CH₃ | Cl | CN | C₂H₅ | S |
| C₂H₅ | Cl | CN | C₂H₅ | S |
| H | H | CN | C₂H₅ | S |
| C₆H₅ | H | CN | C₂H₅ | S |
| CH₃ | H | CN | C₂H₅ | S |
| C₂H₅ | H | CN | C₂H₅ | S |
| H | CH₃ | C≡CH | C₂H₅ | S |
| C₆H₅ | CH₃ | C≡CH | C₂H₅ | S |
| CH₃ | CH₃ | C≡CH | C₂H₅ | S |
| C₂H₅ | CH₃ | C≡CH | C₂H₅ | S |
| H | Cl | C≡CH | C₂H₅ | S |
| C₆H₅ | Cl | C≡CH | C₂H₅ | S |
| CH₃ | Cl | C≡CH | C₂H₅ | S |
| C₂H₅ | Cl | C≡CH | C₂H₅ | S |
| H | H | C≡CH | C₂H₅ | S |
| C₆H₅ | H | C≡CH | C₂H₅ | S |
| CH₃ | H | C≡CH | C₂H₅ | S |
| C₂H₅ | H | C≡CH | C₂H₅ | S |
| H | CH₃ | H | OC₂H₅ | S |
| C₆H₅ | CH₃ | H | OC₂H₅ | S |
| CH₃ | CH₃ | H | OC₂H₅ | S |
| C₂H₅ | CH₃ | H | OC₂H₅ | S |
| H | Cl | H | OC₂H₅ | S |
| C₆H₅ | Cl | H | OC₂H₅ | S |
| CH₃ | Cl | H | OC₂H₅ | S |
| C₂H₅ | Cl | H | OC₂H₅ | S |
| H | H | H | OC₂H₅ | S |
| C₆H₅ | H | H | OC₂H₅ | S |
| CH₃ | H | H | OC₂H₅ | S |
| C₂H₅ | H | H | OC₂H₅ | S |
| H | CH₃ | CN | OC₂H₅ | S |
| C₆H₅ | CH₃ | CN | OC₂H₅ | S |
| CH₃ | CH₃ | CN | OC₂H₅ | S |
| C₂H₅ | CH₃ | CN | OC₂H₅ | S |
| H | Cl | CN | OC₂H₅ | S |
| C₆H₅ | Cl | CN | OC₂H₅ | S |
| CH₃ | Cl | CN | OC₂H₅ | S |
| C₂H₅ | Cl | CN | OC₂H₅ | S |
| H | H | CN | OC₂H₅ | S |
| C₆H₅ | H | CN | OC₂H₅ | S |
| CH₃ | H | CN | OC₂H₅ | S |
| C₂H₅ | H | CN | OC₂H₅ | S |
| H | CH₃ | C≡CH | OC₂H₅ | S |
| C₆H₅ | CH₃ | C≡CH | OC₂H₅ | S |
| CH₃ | CH₃ | C≡CH | OC₂H₅ | S |
| C₂H₅ | CH₃ | C≡CH | OC₂H₅ | S |
| H | Cl | C≡CH | OC₂H₅ | S |
| C₆H₅ | Cl | C≡CH | OC₂H₅ | S |
| CH₃ | Cl | C≡CH | OC₂H₅ | S |

TABLE-continued

| R | R¹ | R² | Rᵃ | X |
|---|---|---|---|---|
| $C_2H_5$ | Cl | C≡CH | $OC_2H_5$ | S |
| H | H | C≡CH | $OC_2H_5$ | S |
| $C_6H_5$ | H | C≡CH | $OC_2H_5$ | S |
| $CH_3$ | H | C≡CH | $OC_2H_5$ | S |
| $C_2H_5$ | H | C≡CH | $OC_2H_5$ | S |
| H | $CH_3$ | H | $CF_3$ | S |
| $C_6H_5$ | $CH_3$ | H | $CF_3$ | S |
| $CH_3$ | $CH_3$ | H | $CF_3$ | S |
| $C_2H_5$ | $CH_3$ | H | $CF_3$ | S |
| H | Cl | H | $CF_3$ | S |
| $C_6H_5$ | Cl | H | $CF_3$ | S |
| $CH_3$ | Cl | H | $CF_3$ | S |
| $C_2H_5$ | Cl | H | $CF_3$ | S |
| H | H | H | $CF_3$ | S |
| $C_6H_5$ | H | H | $CF_3$ | S |
| $CH_3$ | H | H | $CF_3$ | S |
| $C_2H_5$ | H | H | $CF_3$ | S |
| H | $CH_3$ | CN | $CF_3$ | S |
| $C_6H_5$ | $CH_3$ | CN | $CF_3$ | S |
| $CH_3$ | $CH_3$ | CN | $CF_3$ | S |
| $C_2H_5$ | $CH_3$ | CN | $CF_3$ | S |
| H | Cl | CN | $CF_3$ | S |
| $C_6H_5$ | Cl | CN | $CF_3$ | S |
| $CH_3$ | Cl | CN | $CF_3$ | S |
| $C_2H_5$ | Cl | CN | $CF_3$ | S |
| H | H | CN | $CF_3$ | S |
| $C_6H_5$ | H | CN | $CF_3$ | S |
| $CH_3$ | H | CN | $CF_3$ | S |
| $C_2H_5$ | H | CN | $CF_3$ | S |
| H | $CH_3$ | C≡CH | $CF_3$ | S |
| $C_6H_5$ | $CH_3$ | C≡CH | $CF_3$ | S |
| $CH_3$ | $CH_3$ | C≡CH | $CF_3$ | S |
| $C_2H_5$ | $CH_3$ | C≡CH | $CF_3$ | S |
| H | Cl | C≡CH | $CF_3$ | S |
| $C_6H_5$ | Cl | C≡CH | $CF_3$ | S |
| $CH_3$ | Cl | C≡CH | $CF_3$ | S |
| $C_2H_5$ | Cl | C≡CH | $CF_3$ | S |
| H | H | C≡CH | $CF_3$ | S |
| $C_6H_5$ | H | C≡CH | $CF_3$ | S |
| $CH_3$ | H | C≡CH | $CF_3$ | S |
| $C_2H_5$ | H | C≡CH | $CF_3$ | S |
| H | $CH_3$ | H | F | S |
| $C_6H_5$ | $CH_3$ | H | F | S |
| $CH_3$ | $CH_3$ | H | F | S |
| $C_2H_5$ | $CH_3$ | H | F | S |
| H | Cl | H | F | S |
| $C_6H_5$ | Cl | H | F | S |
| $CH_3$ | Cl | H | F | S |
| $C_2H_5$ | Cl | H | F | S |
| H | H | H | F | S |
| $C_6H_5$ | H | H | F | S |
| $CH_3$ | H | H | F | S |
| $C_2H_5$ | H | H | F | S |
| H | $CH_3$ | CN | F | S |
| $C_6H_5$ | $CH_3$ | CN | F | S |
| $CH_3$ | $CH_3$ | CN | F | S |
| $C_2H_5$ | $CH_3$ | CN | F | S |
| H | Cl | CN | F | S |
| $C_6H_5$ | Cl | CN | F | S |
| $CH_3$ | Cl | CN | F | S |
| $C_2H_5$ | Cl | CN | F | S |
| H | H | CN | F | S |
| $C_6H_5$ | H | CN | F | S |
| $CH_3$ | H | CN | F | S |
| $C_2H_5$ | H | CN | F | S |
| H | $CH_3$ | C≡CH | F | S |
| $C_6H_5$ | $CH_3$ | C≡CH | F | S |
| $CH_3$ | $CH_3$ | C≡CH | F | S |
| $C_2H_5$ | $CH_3$ | C≡CH | F | S |
| H | Cl | C≡CH | F | S |
| $C_6H_5$ | Cl | C≡CH | F | S |
| $CH_3$ | Cl | C≡CH | F | S |
| $C_2H_5$ | Cl | C≡CH | F | S |
| H | H | C≡CH | F | S |
| $C_6H_5$ | H | C≡CH | F | S |
| $CH_3$ | H | C≡CH | F | S |
| $C_2H_5$ | H | C≡CH | F | S |
| H | $CH_3$ | H | Cl | S |
| $C_6H_5$ | $CH_3$ | H | Cl | S |
| $CH_3$ | $CH_3$ | H | Cl | S |
| $C_2H_5$ | $CH_3$ | H | Cl | S |
| H | Cl | H | Cl | S |
| $C_6H_5$ | Cl | H | Cl | S |
| $CH_3$ | Cl | H | Cl | S |
| $C_2H_5$ | Cl | H | Cl | S |
| H | H | H | Cl | S |
| $C_6H_5$ | H | H | Cl | S |
| $CH_3$ | H | H | Cl | S |
| $C_2H_5$ | H | H | Cl | S |
| H | $CH_3$ | CN | Cl | S |
| $C_6H_5$ | $CH_3$ | CN | Cl | S |
| $CH_3$ | $CH_3$ | CN | Cl | S |
| $C_2H_5$ | $CH_3$ | CN | Cl | S |
| H | Cl | CN | Cl | S |
| $C_6H_5$ | Cl | CN | Cl | S |
| $CH_3$ | Cl | CN | Cl | S |
| $C_2H_5$ | Cl | CN | Cl | S |
| H | H | CN | Cl | S |
| $C_6H_5$ | H | CN | Cl | S |
| $CH_3$ | H | CN | Cl | S |
| $C_2H_5$ | H | CN | Cl | S |
| H | $CH_3$ | C≡CH | Cl | S |
| $C_6H_5$ | $CH_3$ | C≡CH | Cl | S |
| $CH_3$ | $CH_3$ | C≡CH | Cl | S |
| $C_2H_5$ | $CH_3$ | C≡CH | Cl | S |
| H | Cl | C≡CH | Cl | S |
| $C_6H_5$ | Cl | C≡CH | Cl | S |
| $CH_3$ | Cl | C≡CH | Cl | S |
| $C_2H_5$ | Cl | C≡CH | Cl | S |
| H | H | C≡CH | Cl | S |
| $C_6H_5$ | H | C≡CH | Cl | S |
| $CH_3$ | H | C≡CH | Cl | S |
| $C_2H_5$ | H | C≡CH | Cl | S |
| H | $CH_3$ | H | H | NH |
| $C_6H_5$ | $CH_3$ | H | H | NH |
| $CH_3$ | $CH_3$ | H | H | NH |
| $C_2H_5$ | $CH_3$ | H | H | NH |
| H | Cl | H | H | NH |
| $C_6H_5$ | Cl | H | H | NH |
| $CH_3$ | Cl | H | H | NH |
| $C_2H_5$ | Cl | H | H | NH |
| H | H | H | H | NH |
| $C_6H_5$ | H | H | H | NH |
| $CH_3$ | H | H | H | NH |
| $C_2H_5$ | H | H | H | NH |
| H | $CH_3$ | CN | H | NH |
| $C_6H_5$ | $CH_3$ | CN | H | NH |
| $CH_3$ | $CH_3$ | CN | H | NH |
| $C_2H_5$ | $CH_3$ | CN | H | NH |
| H | Cl | CN | H | NH |
| $C_6H_5$ | Cl | CN | H | NH |
| $CH_3$ | Cl | CN | H | NH |
| $C_2H_5$ | Cl | CN | H | NH |
| H | H | CN | H | NH |
| $C_6H_5$ | H | CN | H | NH |
| $CH_3$ | H | CN | H | NH |
| $C_2H_5$ | H | CN | H | NH |
| H | $CH_3$ | C≡CH | H | NH |
| $C_6H_5$ | $CH_3$ | C≡CH | H | NH |
| $CH_3$ | $CH_3$ | C≡CH | H | NH |
| $C_2H_5$ | $CH_3$ | C≡CH | H | NH |
| H | Cl | C≡CH | H | NH |
| $C_6H_5$ | Cl | C≡CH | H | NH |
| $CH_3$ | Cl | C≡CH | H | NH |
| $C_2H_5$ | Cl | C≡CH | H | NH |
| H | H | C≡CH | H | NH |
| $C_6H_5$ | H | C≡CH | H | NH |
| $CH_3$ | H | C≡CH | H | NH |
| $C_2H_5$ | H | C≡CH | H | NH |
| H | $CH_3$ | H | $CH_3$ | NH |
| $C_6H_5$ | $CH_3$ | H | $CH_3$ | NH |
| $CH_3$ | $CH_3$ | H | $CH_3$ | NH |
| $C_2H_5$ | $CH_3$ | H | $CH_3$ | NH |
| H | Cl | H | $CH_3$ | NH |
| $C_6H_5$ | Cl | H | $CH_3$ | NH |
| $CH_3$ | Cl | H | $CH_3$ | NH |
| $C_2H_5$ | Cl | H | $CH_3$ | NH |
| H | H | H | $CH_3$ | NH |
| $C_6H_5$ | H | H | $CH_3$ | NH |
| $CH_3$ | H | H | $CH_3$ | NH |
| $C_2H_5$ | H | H | $CH_3$ | NH |
| H | $CH_3$ | CN | $CH_3$ | NH |

TABLE-continued

| R | R¹ | R² | Rᵃ | X |
|---|---|---|---|---|
| C₆H₅ | CH₃ | CN | CH₃ | NH |
| CH₃ | CH₃ | CN | CH₃ | NH |
| C₂H₅ | CH₃ | CN | CH₃ | NH |
| H | Cl | CN | CH₃ | NH |
| C₆H₅ | Cl | CN | CH₃ | NH |
| CH₃ | Cl | CN | CH₃ | NH |
| C₂H₅ | Cl | CN | CH₃ | NH |
| H | H | CN | CH₃ | NH |
| C₆H₅ | H | CN | CH₃ | NH |
| CH₃ | H | CN | CH₃ | NH |
| C₂H₅ | H | CN | CH₃ | NH |
| H | CH₃ | C≡CH | CH₃ | NH |
| C₆H₅ | CH₃ | C≡CH | CH₃ | NH |
| CH₃ | CH₃ | C≡CH | CH₃ | NH |
| C₂H₅ | CH₃ | C≡CH | CH₃ | NH |
| H | Cl | C≡CH | CH₃ | NH |
| C₆H₅ | Cl | C≡CH | CH₃ | NH |
| CH₃ | Cl | C≡CH | CH₃ | NH |
| C₂H₅ | Cl | C≡CH | CH₃ | NH |
| H | H | C≡CH | CH₃ | NH |
| C₆H₅ | H | C≡CH | CH₃ | NH |
| CH₃ | H | C≡CH | CH₃ | NH |
| C₂H₅ | H | C≡CH | CH₃ | NH |
| H | CH₃ | H | OCH₃ | NH |
| C₆H₅ | CH₃ | H | OCH₃ | NH |
| CH₃ | CH₃ | H | OCH₃ | NH |
| C₂H₅ | CH₃ | H | OCH₃ | NH |
| H | Cl | H | OCH₃ | NH |
| C₆H₅ | Cl | H | OCH₃ | NH |
| CH₃ | Cl | H | OCH₃ | NH |
| C₂H₅ | Cl | H | OCH₃ | NH |
| H | H | H | OCH₃ | NH |
| C₆H₅ | H | H | OCH₃ | NH |
| CH₃ | H | H | OCH₃ | NH |
| C₂H₅ | H | H | OCH₃ | NH |
| H | CH₃ | CN | OCH₃ | NH |
| C₆H₅ | CH₃ | CN | OCH₃ | NH |
| CH₃ | CH₃ | CN | OCH₃ | NH |
| C₂H₅ | CH₃ | CN | OCH₃ | NH |
| H | Cl | CN | OCH₃ | NH |
| C₆H₅ | Cl | CN | OCH₃ | NH |
| CH₃ | Cl | CN | OCH₃ | NH |
| C₂H₅ | Cl | CN | OCH₃ | NH |
| H | H | CN | OCH₃ | NH |
| C₆H₅ | H | CN | OCH₃ | NH |
| CH₃ | H | CN | OCH₃ | NH |
| C₂H₅ | H | CN | OCH₃ | NH |
| H | CH₃ | C≡CH | OCH₃ | NH |
| C₆H₅ | CH₃ | C≡CH | OCH₃ | NH |
| CH₃ | CH₃ | C≡CH | OCH₃ | NH |
| C₂H₅ | CH₃ | C≡CH | OCH₃ | NH |
| H | Cl | C≡CH | OCH₃ | NH |
| C₆H₅ | Cl | C≡CH | OCH₃ | NH |
| CH₃ | Cl | C≡CH | OCH₃ | NH |
| C₂H₅ | Cl | C≡CH | OCH₃ | NH |
| H | H | C≡CH | OCH₃ | NH |
| C₆H₅ | H | C≡CH | OCH₃ | NH |
| CH₃ | H | C≡CH | OCH₃ | NH |
| C₂H₅ | H | C≡CH | OCH₃ | NH |
| H | CH₃ | H | C₂H₅ | NH |
| C₆H₅ | CH₃ | H | C₂H₅ | NH |
| CH₃ | CH₃ | H | C₂H₅ | NH |
| C₂H₅ | CH₃ | H | C₂H₅ | NH |
| H | Cl | H | C₂H₅ | NH |
| C₆H₅ | Cl | H | C₂H₅ | NH |
| CH₃ | Cl | H | C₂H₅ | NH |
| C₂H₅ | Cl | H | C₂H₅ | NH |
| H | H | H | C₂H₅ | NH |
| C₆H₅ | H | H | C₂H₅ | NH |
| CH₃ | H | H | C₂H₅ | NH |
| C₂H₅ | H | H | C₂H₅ | NH |
| H | CH₃ | CN | C₂H₅ | NH |
| C₆H₅ | CH₃ | CN | C₂H₅ | NH |
| CH₃ | CH₃ | CN | C₂H₅ | NH |
| C₂H₅ | CH₃ | CN | C₂H₅ | NH |
| H | Cl | CN | C₂H₅ | NH |
| C₆H₅ | Cl | CN | C₂H₅ | NH |
| CH₃ | Cl | CN | C₂H₅ | NH |
| C₂H₅ | Cl | CN | C₂H₅ | NH |
| H | H | CN | C₂H₅ | NH |
| C₆H₅ | H | CN | C₂H₅ | NH |
| CH₃ | H | CN | C₂H₅ | NH |
| C₂H₅ | H | CN | C₂H₅ | NH |
| H | CH₃ | C≡CH | C₂H₅ | NH |
| C₆H₅ | CH₃ | C≡CH | C₂H₅ | NH |
| CH₃ | CH₃ | C≡CH | C₂H₅ | NH |
| C₂H₅ | CH₃ | C≡CH | C₂H₅ | NH |
| H | Cl | C≡CH | C₂H₅ | NH |
| C₆H₅ | Cl | C≡CH | C₂H₅ | NH |
| CH₃ | Cl | C≡CH | C₂H₅ | NH |
| C₂H₅ | Cl | C≡CH | C₂H₅ | NH |
| H | H | C≡CH | C₂H₅ | NH |
| C₆H₅ | H | C≡CH | C₂H₅ | NH |
| CH₃ | H | C≡CH | C₂H₅ | NH |
| C₂H₅ | H | C≡CH | C₂H₅ | NH |
| H | CH₃ | H | OC₂H₅ | NH |
| C₆H₅ | CH₃ | H | OC₂H₅ | NH |
| CH₃ | CH₃ | H | OC₂H₅ | NH |
| C₂H₅ | CH₃ | H | OC₂H₅ | NH |
| H | Cl | H | OC₂H₅ | NH |
| C₆H₅ | Cl | H | OC₂H₅ | NH |
| CH₃ | Cl | H | OC₂H₅ | NH |
| C₂H₅ | Cl | H | OC₂H₅ | NH |
| H | H | H | OC₂H₅ | NH |
| C₆H₅ | H | H | OC₂H₅ | NH |
| CH₃ | H | H | OC₂H₅ | NH |
| C₂H₅ | H | H | OC₂H₅ | NH |
| H | CH₃ | CN | OC₂H₅ | NH |
| C₆H₅ | CH₃ | CN | OC₂H₅ | NH |
| CH₃ | CH₃ | CN | OC₂H₅ | NH |
| C₂H₅ | CH₃ | CN | OC₂H₅ | NH |
| H | Cl | CN | OC₂H₅ | NH |
| C₆H₅ | Cl | CN | OC₂H₅ | NH |
| CH₃ | Cl | CN | OC₂H₅ | NH |
| C₂H₅ | Cl | CN | OC₂H₅ | NH |
| H | H | CN | OC₂H₅ | NH |
| C₆H₅ | H | CN | OC₂H₅ | NH |
| CH₃ | H | CN | OC₂H₅ | NH |
| C₂H₅ | H | CN | OC₂H₅ | NH |
| H | CH₃ | C≡CH | OC₂H₅ | NH |
| C₆H₅ | CH₃ | C≡CH | OC₂H₅ | NH |
| CH₃ | CH₃ | C≡CH | OC₂H₅ | NH |
| C₂H₅ | CH₃ | C≡CH | OC₂H₅ | NH |
| H | Cl | C≡CH | OC₂H₅ | NH |
| C₆H₅ | Cl | C≡CH | OC₂H₅ | NH |
| CH₃ | Cl | C≡CH | OC₂H₅ | NH |
| C₂H₅ | Cl | C≡CH | OC₂H₅ | NH |
| H | H | C≡CH | OC₂H₅ | NH |
| C₆H₅ | H | C≡CH | OC₂H₅ | NH |
| CH₃ | H | C≡CH | OC₂H₅ | NH |
| C₂H₅ | H | C≡CH | OC₂H₅ | NH |
| H | CH₃ | H | CF₃ | NH |
| C₆H₅ | CH₃ | H | CF₃ | NH |
| CH₃ | CH₃ | H | CF₃ | NH |
| C₂H₅ | CH₃ | H | CF₃ | NH |
| H | Cl | H | CF₃ | NH |
| C₆H₅ | Cl | H | CF₃ | NH |
| CH₃ | Cl | H | CF₃ | NH |
| C₂H₅ | Cl | H | CF₃ | NH |
| H | H | H | CF₃ | NH |
| C₆H₅ | H | H | CF₃ | NH |
| CH₃ | H | H | CF₃ | NH |
| C₂H₅ | H | H | CF₃ | NH |
| H | CH₃ | CN | CF₃ | NH |
| C₆H₅ | CH₃ | CN | CF₃ | NH |
| CH₃ | CH₃ | CN | CF₃ | NH |
| C₂H₅ | CH₃ | CN | CF₃ | NH |
| H | Cl | CN | CF₃ | NH |
| C₆H₅ | Cl | CN | CF₃ | NH |
| CH₃ | Cl | CN | CF₃ | NH |
| C₂H₅ | Cl | CN | CF₃ | NH |
| H | H | CN | CF₃ | NH |
| C₆H₅ | H | CN | CF₃ | NH |
| CH₃ | H | CN | CF₃ | NH |
| C₂H₅ | H | CN | CF₃ | NH |
| H | CH₃ | C≡CH | CF₃ | NH |
| C₆H₅ | CH₃ | C≡CH | CF₃ | NH |
| CH₃ | CH₃ | C≡CH | CF₃ | NH |
| C₂H₅ | CH₃ | C≡CH | CF₃ | NH |
| H | Cl | C≡CH | CF₃ | NH |
| C₆H₅ | Cl | C≡CH | CF₃ | NH |
| CH₃ | Cl | C≡CH | CF₃ | NH |

TABLE-continued

| R | R¹ | R² | $R^a$ | X |
|---|---|---|---|---|
| C₂H₅ | Cl | C≡CH | CF₃ | NH |
| H | H | C≡CH | CF₃ | NH |
| C₆H₅ | H | C≡CH | CF₃ | NH |
| CH₃ | H | C≡CH | CF₃ | NH |
| C₂H₅ | H | C≡CH | CF₃ | NH |
| H | CH₃ | H | F | NH |
| C₆H₅ | CH₃ | H | F | NH |
| CH₃ | CH₃ | H | F | NH |
| C₂H₅ | CH₃ | H | F | NH |
| H | Cl | H | F | NH |
| C₆H₅ | Cl | H | F | NH |
| CH₃ | Cl | H | F | NH |
| C₂H₅ | Cl | H | F | NH |
| H | H | H | F | NH |
| C₆H₅ | H | H | F | NH |
| CH₃ | H | H | F | NH |
| C₂H₅ | H | H | F | NH |
| H | CH₃ | CN | F | NH |
| C₆H₅ | CH₃ | CN | F | NH |
| CH₃ | CH₃ | CN | F | NH |
| C₂H₅ | CH₃ | CN | F | NH |
| H | Cl | CN | F | NH |
| C₆H₅ | Cl | CN | F | NH |
| CH₃ | Cl | CN | F | NH |
| C₂H₅ | Cl | CN | F | NH |
| H | H | CN | F | NH |
| C₆H₅ | H | CN | F | NH |
| CH₃ | H | CN | F | NH |
| C₂H₅ | H | CN | F | NH |
| H | CH₃ | C≡CH | F | NH |
| C₆H₅ | CH₃ | C≡CH | F | NH |
| CH₃ | CH₃ | C≡CH | F | NH |
| C₂H₅ | CH₃ | C≡CH | F | NH |
| H | Cl | C≡CH | F | NH |
| C₆H₅ | Cl | C≡CH | F | NH |
| CH₃ | Cl | C≡CH | F | NH |
| C₂H₅ | Cl | C≡CH | F | NH |
| H | H | C≡CH | F | NH |
| C₆H₅ | H | C≡CH | F | NH |
| CH₃ | H | C≡CH | F | NH |
| C₂H₅ | H | C≡CH | F | NH |
| H | CH₃ | H | Cl | NH |
| C₆H₅ | CH₃ | H | Cl | NH |
| CH₃ | CH₃ | H | Cl | NH |
| C₂H₅ | CH₃ | H | Cl | NH |
| H | Cl | H | Cl | NH |
| C₆H₅ | Cl | H | Cl | NH |
| CH₃ | Cl | H | Cl | NH |
| C₂H₅ | Cl | H | Cl | NH |
| H | H | H | Cl | NH |
| C₆H₅ | H | H | Cl | NH |
| CH₃ | H | H | Cl | NH |
| C₂H₅ | H | H | Cl | NH |
| H | CH₃ | CN | Cl | NH |
| C₆H₅ | CH₃ | CN | Cl | NH |
| CH₃ | CH₃ | CN | Cl | NH |
| C₂H₅ | CH₃ | CN | Cl | NH |
| H | Cl | CN | Cl | NH |
| C₆H₅ | Cl | CN | Cl | NH |
| CH₃ | Cl | CN | Cl | NH |
| C₂H₅ | Cl | CN | Cl | NH |
| H | H | CN | Cl | NH |
| C₆H₅ | H | CN | Cl | NH |
| CH₃ | H | CN | Cl | NH |
| C₂H₅ | H | CN | Cl | NH |
| H | CH₃ | C≡CH | Cl | NH |
| C₆H₅ | CH₃ | C≡CH | Cl | NH |
| CH₃ | CH₃ | C≡CH | Cl | NH |
| C₂H₅ | CH₃ | C≡CH | Cl | NH |
| H | Cl | C≡CH | Cl | NH |
| C₆H₅ | Cl | C≡CH | Cl | NH |
| CH₃ | Cl | C≡CH | Cl | NH |
| C₂H₅ | Cl | C≡CH | Cl | NH |
| H | H | C≡CH | Cl | NH |
| C₆H₅ | H | C≡CH | Cl | NH |
| CH₃ | H | C≡CH | Cl | NH |
| C₂H₅ | H | C≡CH | Cl | NH |
| H | CH₃ | H | H | CH₂ |
| C₆H₅ | CH₃ | H | H | CH₂ |
| CH₃ | CH₃ | H | H | CH₂ |
| C₂H₅ | CH₃ | H | H | CH₂ |
| H | Cl | H | H | CH₂ |
| C₆H₅ | Cl | H | H | CH₂ |
| CH₃ | Cl | H | H | CH₂ |
| C₂H₅ | Cl | H | H | CH₂ |
| H | H | H | H | CH₂ |
| C₆H₅ | H | H | H | CH₂ |
| CH₃ | H | H | H | CH₂ |
| C₂H₅ | H | H | H | CH₂ |
| H | CH₃ | CN | H | CH₂ |
| C₆H₅ | CH₃ | CN | H | CH₂ |
| CH₃ | CH₃ | CN | H | CH₂ |
| C₂H₅ | CH₃ | CN | H | CH₂ |
| H | Cl | CN | H | CH₂ |
| C₆H₅ | Cl | CN | H | CH₂ |
| CH₃ | Cl | CN | H | CH₂ |
| C₂H₅ | Cl | CN | H | CH₂ |
| H | H | CN | H | CH₂ |
| C₆H₅ | H | CN | H | CH₂ |
| CH₃ | H | CN | H | CH₂ |
| C₂H₅ | H | CN | H | CH₂ |
| H | CH₃ | C≡CH | H | CH₂ |
| C₆H₅ | CH₃ | C≡CH | H | CH₂ |
| CH₃ | CH₃ | C≡CH | H | CH₂ |
| C₂H₅ | CH₃ | C≡CH | H | CH₂ |
| H | Cl | C≡CH | H | CH₂ |
| C₆H₅ | Cl | C≡CH | H | CH₂ |
| CH₃ | Cl | C≡CH | H | CH₂ |
| C₂H₅ | Cl | C≡CH | H | CH₂ |
| H | H | C≡CH | H | CH₂ |
| C₆H₅ | H | C≡CH | H | CH₂ |
| CH₃ | H | C≡CH | H | CH₂ |
| C₂H₅ | H | C≡CH | H | CH₂ |
| H | CH₃ | H | CH₃ | CH₂ |
| C₆H₅ | CH₃ | H | CH₃ | CH₂ |
| CH₃ | CH₃ | H | CH₃ | CH₂ |
| C₂H₅ | CH₃ | H | CH₃ | CH₂ |
| H | Cl | H | CH₃ | CH₂ |
| C₆H₅ | Cl | H | CH₃ | CH₂ |
| CH₃ | Cl | H | CH₃ | CH₂ |
| C₂H₅ | Cl | H | CH₃ | CH₂ |
| H | H | H | CH₃ | CH₂ |
| C₆H₅ | H | H | CH₃ | CH₂ |
| CH₃ | H | H | CH₃ | CH₂ |
| C₂H₅ | H | H | CH₃ | CH₂ |
| H | CH₃ | CN | CH₃ | CH₂ |
| C₆H₅ | CH₃ | CN | CH₃ | CH₂ |
| CH₃ | CH₃ | CN | CH₃ | CH₂ |
| C₂H₅ | CH₃ | CN | CH₃ | CH₂ |
| H | Cl | CN | CH₃ | CH₂ |
| C₆H₅ | Cl | CN | CH₃ | CH₂ |
| CH₃ | Cl | CN | CH₃ | CH₂ |
| C₂H₅ | Cl | CN | CH₃ | CH₂ |
| H | H | CN | CH₃ | CH₂ |
| C₆H₅ | H | CN | CH₃ | CH₂ |
| CH₃ | H | CN | CH₃ | CH₂ |
| C₂H₅ | H | CN | CH₃ | CH₂ |
| H | CH₃ | C≡CH | CH₃ | CH₂ |
| C₆H₅ | CH₃ | C≡CH | CH₃ | CH₂ |
| CH₃ | CH₃ | C≡CH | CH₃ | CH₂ |
| C₂H₅ | CH₃ | C≡CH | CH₃ | CH₂ |
| H | Cl | C≡CH | CH₃ | CH₂ |
| C₆H₅ | Cl | C≡CH | CH₃ | CH₂ |
| CH₃ | Cl | C≡CH | CH₃ | CH₂ |
| C₂H₅ | Cl | C≡CH | CH₃ | CH₂ |
| H | H | C≡CH | CH₃ | CH₂ |
| C₆H₅ | H | C≡CH | CH₃ | CH₂ |
| CH₃ | H | C≡CH | CH₃ | CH₂ |
| C₂H₅ | H | C≡CH | CH₃ | CH₂ |
| H | CH₃ | H | OCH₃ | CH₂ |
| C₆H₅ | CH₃ | H | OCH₃ | CH₂ |
| CH₃ | CH₃ | H | OCH₃ | CH₂ |
| C₂H₅ | CH₃ | H | OCH₃ | CH₂ |
| H | Cl | H | OCH₃ | CH₂ |
| C₆H₅ | Cl | H | OCH₃ | CH₂ |
| CH₃ | Cl | H | OCH₃ | CH₂ |
| C₂H₅ | Cl | H | OCH₃ | CH₂ |
| H | H | H | OCH₃ | CH₂ |
| C₆H₅ | H | H | OCH₃ | CH₂ |
| CH₃ | H | H | OCH₃ | CH₂ |
| C₂H₅ | H | H | OCH₃ | CH₂ |
| H | CH₃ | CN | OCH₃ | CH₂ |

TABLE-continued

| R | R¹ | R² | Rᵃ | X |
|---|---|---|---|---|
| C₆H₅ | CH₃ | CN | OCH₃ | CH₂ |
| CH₃ | CH₃ | CN | OCH₃ | CH₂ |
| C₂H₅ | CH₃ | CN | OCH₃ | CH₂ |
| H | Cl | CN | OCH₃ | CH₂ |
| C₆H₅ | Cl | CN | OCH₃ | CH₂ |
| CH₃ | Cl | CN | OCH₃ | CH₂ |
| C₂H₅ | Cl | CN | OCH₃ | CH₂ |
| H | H | CN | OCH₃ | CH₂ |
| C₆H₅ | H | CN | OCH₃ | CH₂ |
| CH₃ | H | CN | OCH₃ | CH₂ |
| C₂H₅ | H | CN | OCH₃ | CH₂ |
| H | CH₃ | C≡CH | OCH₃ | CH₂ |
| C₆H₅ | CH₃ | C≡CH | OCH₃ | CH₂ |
| CH₃ | CH₃ | C≡CH | OCH₃ | CH₂ |
| C₂H₅ | CH₃ | C≡CH | OCH₃ | CH₂ |
| H | Cl | C≡CH | OCH₃ | CH₂ |
| C₆H₅ | Cl | C≡CH | OCH₃ | CH₂ |
| CH₃ | Cl | C≡CH | OCH₃ | CH₂ |
| C₂H₅ | Cl | C≡CH | OCH₃ | CH₂ |
| H | H | C≡CH | OCH₃ | CH₂ |
| C₆H₅ | H | C≡CH | OCH₃ | CH₂ |
| CH₃ | H | C≡CH | OCH₃ | CH₂ |
| C₂H₅ | H | C≡CH | OCH₃ | CH₂ |
| H | CH₃ | H | C₂H₅ | CH₂ |
| C₆H₅ | CH₃ | H | C₂H₅ | CH₂ |
| CH₃ | CH₃ | H | C₂H₅ | CH₂ |
| C₂H₅ | CH₃ | H | C₂H₅ | CH₂ |
| H | Cl | H | C₂H₅ | CH₂ |
| C₆H₅ | Cl | H | C₂H₅ | CH₂ |
| CH₃ | Cl | H | C₂H₅ | CH₂ |
| C₂H₅ | Cl | H | C₂H₅ | CH₂ |
| H | H | H | C₂H₅ | CH₂ |
| C₆H₅ | H | H | C₂H₅ | CH₂ |
| CH₃ | H | H | C₂H₅ | CH₂ |
| C₂H₅ | H | H | C₂H₅ | CH₂ |
| H | CH₃ | CN | C₂H₅ | CH₂ |
| C₆H₅ | CH₃ | CN | C₂H₅ | CH₂ |
| CH₃ | CH₃ | CN | C₂H₅ | CH₂ |
| C₂H₅ | CH₃ | CN | C₂H₅ | CH₂ |
| H | Cl | CN | C₂H₅ | CH₂ |
| C₆H₅ | Cl | CN | C₂H₅ | CH₂ |
| CH₃ | Cl | CN | C₂H₅ | CH₂ |
| C₂H₅ | Cl | CN | C₂H₅ | CH₂ |
| H | H | CN | C₂H₅ | CH₂ |
| C₆H₅ | H | CN | C₂H₅ | CH₂ |
| CH₃ | H | CN | C₂H₅ | CH₂ |
| C₂H₅ | H | CN | C₂H₅ | CH₂ |
| H | CH₃ | C≡CH | C₂H₅ | CH₂ |
| C₆H₅ | CH₃ | C≡CH | C₂H₅ | CH₂ |
| CH₃ | CH₃ | C≡CH | C₂H₅ | CH₂ |
| C₂H₅ | CH₃ | C≡CH | C₂H₅ | CH₂ |
| H | Cl | C≡CH | C₂H₅ | CH₂ |
| C₆H₅ | Cl | C≡CH | C₂H₅ | CH₂ |
| CH₃ | Cl | C≡CH | C₂H₅ | CH₂ |
| C₂H₅ | Cl | C≡CH | C₂H₅ | CH₂ |
| H | H | C≡CH | C₂H₅ | CH₂ |
| C₆H₅ | H | C≡CH | C₂H₅ | CH₂ |
| CH₃ | H | C≡CH | C₂H₅ | CH₂ |
| C₂H₅ | H | C≡CH | C₂H₅ | CH₂ |
| H | CH₃ | H | OC₂H₅ | CH₂ |
| C₆H₅ | CH₃ | H | OC₂H₅ | CH₂ |
| CH₃ | CH₃ | H | OC₂H₅ | CH₂ |
| C₂H₅ | CH₃ | H | OC₂H₅ | CH₂ |
| H | Cl | H | OC₂H₅ | CH₂ |
| C₆H₅ | Cl | H | OC₂H₅ | CH₂ |
| CH₃ | Cl | H | OC₂H₅ | CH₂ |
| C₂H₅ | Cl | H | OC₂H₅ | CH₂ |
| H | H | H | OC₂H₅ | CH₂ |
| C₆H₅ | H | H | OC₂H₅ | CH₂ |
| CH₃ | H | H | OC₂H₅ | CH₂ |
| C₂H₅ | H | H | OC₂H₅ | CH₂ |
| H | CH₃ | CN | OC₂H₅ | CH₂ |
| C₆H₅ | CH₃ | CN | OC₂H₅ | CH₂ |
| CH₃ | CH₃ | CN | OC₂H₅ | CH₂ |
| C₂H₅ | CH₃ | CN | OC₂H₅ | CH₂ |
| H | Cl | CN | OC₂H₅ | CH₂ |
| C₆H₅ | Cl | CN | OC₂H₅ | CH₂ |
| CH₃ | Cl | CN | OC₂H₅ | CH₂ |
| C₂H₅ | Cl | CN | OC₂H₅ | CH₂ |
| H | H | CN | OC₂H₅ | CH₂ |
| C₆H₅ | H | CN | OC₂H₅ | CH₂ |
| CH₃ | H | CN | OC₂H₅ | CH₂ |
| C₂H₅ | H | CN | OC₂H₅ | CH₂ |
| H | CH₃ | C≡CH | OC₂H₅ | CH₂ |
| C₆H₅ | CH₃ | C≡CH | OC₂H₅ | CH₂ |
| CH₃ | CH₃ | C≡CH | OC₂H₅ | CH₂ |
| C₂H₅ | CH₃ | C≡CH | OC₂H₅ | CH₂ |
| H | Cl | C≡CH | OC₂H₅ | CH₂ |
| C₆H₅ | Cl | C≡CH | OC₂H₅ | CH₂ |
| CH₃ | Cl | C≡CH | OC₂H₅ | CH₂ |
| C₂H₅ | Cl | C≡CH | OC₂H₅ | CH₂ |
| H | H | C≡CH | OC₂H₅ | CH₂ |
| C₆H₅ | H | C≡CH | OC₂H₅ | CH₂ |
| CH₃ | H | C≡CH | OC₂H₅ | CH₂ |
| C₂H₅ | H | C≡CH | OC₂H₅ | CH₂ |
| H | CH₃ | H | CF₃ | CH₂ |
| C₆H₅ | CH₃ | H | CF₃ | CH₂ |
| CH₃ | CH₃ | H | CF₃ | CH₂ |
| C₂H₅ | CH₃ | H | CF₃ | CH₂ |
| H | Cl | H | CF₃ | CH₂ |
| C₆H₅ | Cl | H | CF₃ | CH₂ |
| CH₃ | Cl | H | CF₃ | CH₂ |
| C₂H₅ | Cl | H | CF₃ | CH₂ |
| H | H | H | CF₃ | CH₂ |
| C₆H₅ | H | H | CF₃ | CH₂ |
| CH₃ | H | H | CF₃ | CH₂ |
| C₂H₅ | H | H | CF₃ | CH₂ |
| H | CH₃ | CN | CF₃ | CH₂ |
| C₆H₅ | CH₃ | CN | CF₃ | CH₂ |
| CH₃ | CH₃ | CN | CF₃ | CH₂ |
| C₂H₅ | CH₃ | CN | CF₃ | CH₂ |
| H | Cl | CN | CF₃ | CH₂ |
| C₆H₅ | Cl | CN | CF₃ | CH₂ |
| CH₃ | Cl | CN | CF₃ | CH₂ |
| C₂H₅ | Cl | CN | CF₃ | CH₂ |
| H | H | CN | CF₃ | CH₂ |
| C₆H₅ | H | CN | CF₃ | CH₂ |
| CH₃ | H | CN | CF₃ | CH₂ |
| C₂H₅ | H | CN | CF₃ | CH₂ |
| H | CH₃ | C≡CH | CF₃ | CH₂ |
| C₆H₅ | CH₃ | C≡CH | CF₃ | CH₂ |
| CH₃ | CH₃ | C≡CH | CF₃ | CH₂ |
| C₂H₅ | CH₃ | C≡CH | CF₃ | CH₂ |
| H | Cl | C≡CH | CF₃ | CH₂ |
| C₆H₅ | Cl | C≡CH | CF₃ | CH₂ |
| CH₃ | Cl | C≡CH | CF₃ | CH₂ |
| C₂H₅ | Cl | C≡CH | CF₃ | CH₂ |
| H | H | C≡CH | CF₃ | CH₂ |
| C₆H₅ | H | C≡CH | CF₃ | CH₂ |
| CH₃ | H | C≡CH | CF₃ | CH₂ |
| C₂H₅ | H | C≡CH | CF₃ | CH₂ |
| H | CH₃ | H | F | CH₂ |
| C₆H₅ | CH₃ | H | F | CH₂ |
| CH₃ | CH₃ | H | F | CH₂ |
| C₂H₅ | CH₃ | H | F | CH₂ |
| H | Cl | H | F | CH₂ |
| C₆H₅ | Cl | H | F | CH₂ |
| CH₃ | Cl | H | F | CH₂ |
| C₂H₅ | Cl | H | F | CH₂ |
| H | H | H | F | CH₂ |
| C₆H₅ | H | H | F | CH₂ |
| CH₃ | H | H | F | CH₂ |
| C₂H₅ | H | H | F | CH₂ |
| H | CH₃ | CN | F | CH₂ |
| C₆H₅ | CH₃ | CN | F | CH₂ |
| CH₃ | CH₃ | CN | F | CH₂ |
| C₂H₅ | CH₃ | CN | F | CH₂ |
| H | Cl | CN | F | CH₂ |
| C₆H₅ | Cl | CN | F | CH₂ |
| CH₃ | Cl | CN | F | CH₂ |
| C₂H₅ | Cl | CN | F | CH₂ |
| H | H | CN | F | CH₂ |
| C₆H₅ | H | CN | F | CH₂ |
| CH₃ | H | CN | F | CH₂ |
| C₂H₅ | H | CN | F | CH₂ |
| H | CH₃ | C≡CH | F | CH₂ |
| C₆H₅ | CH₃ | C≡CH | F | CH₂ |
| CH₃ | CH₃ | C≡CH | F | CH₂ |
| C₂H₅ | CH₃ | C≡CH | F | CH₂ |
| H | Cl | C≡CH | F | CH₂ |
| C₆H₅ | Cl | C≡CH | F | CH₂ |
| CH₃ | Cl | C≡CH | F | CH₂ |

TABLE-continued

| R | R¹ | R² | Rᵃ | X |
|---|---|---|---|---|
| C₂H₅ | Cl | C═CH | F | CH₂ |
| H | H | C═CH | F | CH₂ |
| C₆H₅ | H | C═CH | F | CH₂ |
| CH₃ | H | C═CH | F | CH₂ |
| C₂H₅ | H | C═CH | F | CH₂ |
| H | CH₃ | H | Cl | CH₂ |
| C₆H₅ | CH₃ | H | Cl | CH₂ |
| CH₃ | CH₃ | H | Cl | CH₂ |
| C₂H₅ | CH₃ | H | Cl | CH₂ |
| H | Cl | H | Cl | CH₂ |
| C₆H₅ | Cl | H | Cl | CH₂ |
| CH₃ | Cl | H | Cl | CH₂ |
| C₂H₅ | Cl | H | Cl | CH₂ |
| H | H | H | Cl | CH₂ |
| C₆H₅ | H | H | Cl | CH₂ |
| CH₃ | H | H | Cl | CH₂ |
| C₂H₅ | H | H | Cl | CH₂ |
| H | CH₃ | CN | Cl | CH₂ |
| C₆H₅ | CH₃ | CN | Cl | CH₂ |
| CH₃ | CN₃ | CN | Cl | CH₂ |
| C₂H₅ | CH₃ | CN | Cl | CH₂ |
| H | Cl | CN | Cl | CH₂ |
| C₆H₅ | Cl | CN | Cl | CH₂ |
| CH₃ | Cl | CN | Cl | CH₂ |
| C₂H₅ | Cl | CN | Cl | CH₂ |
| H | H | CN | Cl | CH₂ |
| C₆H₅ | H | CN | Cl | CH₂ |
| CH₃ | H | CN | Cl | CH₂ |
| C₂H₅ | H | CN | Cl | CH₂ |
| H | CH₃ | C═CH | Cl | CH₂ |
| C₆H₅ | CH₃ | C═CH | Cl | CH₂ |
| CH₃ | CH₃ | C═CH | Cl | CH₂ |
| C₂H₅ | CH₃ | C═CH | Cl | CH₂ |
| H | Cl | C═CH | Cl | CH₂ |
| C₆H₅ | Cl | C═CH | Cl | CH₂ |
| CH₃ | Cl | C═CH | Cl | CH₂ |
| C₂H₅ | Cl | C═CH | Cl | CH₂ |
| H | H | C═CH | Cl | CH₂ |
| C₆H₅ | H | C═CH | Cl | CH₂ |
| CH₃ | H | C═CH | Cl | CH₂ |
| C₂H₅ | H | C═CH | Cl | CH₂ |

The compounds of the formulae Ia and Ib are suitable for effectively controlling pests from the class of the insects, arachnids and nematodes. They can be used as pesticides in crop protection and in the hygiene, material protection and veterinary sectors.

The insect pests include, from the order of the butterflies (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* from the order of the beetles (Coleoptera), for example *Agrilus sinuatus, Agriotes lineatus, Agriotes obscurus, Amphimallus solstitialis, Anisancrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vesoertinus, Crioceris asparagi, Diabrotica lonoicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typoqraphus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria;* from the order of the Diptera, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* from the order of the Thysanoptera, for example *Frankliniella fusca, Frankliniella occidentalis, Frankliniella tritici, Scirtothrips citri, Thrips oryzae, Thrips palmi* and *Thrips tabaci;* from the order of the Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta;* from the order of the Heteroptera, for example *Acrosternum hilare, Blissus leucopterus, Cyrtopeltis notatus, Dysdercus cinqulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor;* from the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Mvzodes oersicae, Mvzus cerasi, Nilaoarvata lugens, Penphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii;* from the order of the Isoptera, for example *Calotermes flavicollis, Leucotermes flavipes, Reticulitermes lucifugus* and *Termes natalensis;* from the order of the Orthoptera, for example *Acheta domestica, Blatta orientalis, Blatella germanica, Forficula auricularia, Gryllotaloa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Periolaneta americana, Schistocerca americana, Schistocerca peregrina, Stauronotus maroccanus* and *Tachycines asynamorus;* from the class of the Arachnoidea, for example Acarina, such as *Amblyomma americanum, Amblyomma variegatum, Argas persicus, Boophilus annulatus, Boophilus decolaratus, Boophilus microplus, Brevipalpus phoenicis, Bryobia praetiosa, Dermacentor silvarum, Eotetranychus carpini, Eriophyes sheldoni, Hyalomma trucatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae;* from the class of the nematodes, for example root gall nematodes, e.g. *Meloidogyne hapla, Meloidogyne incognita* and *Meloidogyne javanica,* cyst-forming nematodes, e.g. *Globodera rostochiensis, Heterodera avenae, Heterodera glycinae, Heterodera schatii, Heterodera trifolii,* and stem and leaf eelworms, e.g. *Belonolaimus longicaudatus, Ditylenchus destructor, Ditylenchus dipsaci, Heliocotylenchus multicinctus, Longidorus elongatus, Radopholus similis, Rotylenchus roousrus, Trichodorus primitivus, Tylenchorhynchus claytoni, Tylencnorhynchus dubius, Pratylenchus neglectus, Pratylenchus penetrans, Pratylenchus curvitatus* and *Pratylenchus goodeyi.*

The active ingredients can be used as such, in the form of their formulations or the application forms prepared therefrom, for example in the form of directly sprayable solutions, powders, suspensions or dispersions, emulsions, oil dispersions, pastes, dusting agents, broadcasting agents or granules, by spraying, nebulizing, dusting, broadcasting or pouring. The application forms depend entirely on the intended uses; they should in any case ensure very fine distribution of the novel active ingredients.

Mineral oil fractions boiling within a medium to high range, such as kerosene or diesel oil, and coal tar oils and oils of animal or vegetable origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone or water, are suitable for the preparation of directly sprayable solutions, emulsions, pastes or oil dispersions.

Aqueous application forms can be prepared from emulsion concentrates, pastes, wettable powders or oil dispersions by adding water. For the preparation of emulsions, pastes or oil dispersions, the substances, as such or dissolved in an oil or solvent, can be homogenized in water by means of wetting agents, adherents, dispersants or emulsifiers. However, concentrates which consist of active ingredient, wetting agents, adherents, dispersants of emulsifiers and possibly solvents or oil and which are suitable for dilution with water can also be prepared.

Suitable surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and alkali metal and alkaline earth metal salts thereof, salts of sulfated fatty alcohol glycol ethers, condensates of sulfonated naphthalene derivatives with formaldehyde, condensates of naphthalene or of naphthalenesulfonic acid with phenol and formaldehyde, polyoxyethylene octylphenol ether, ethoxylated isooctylphenol, ocytlphenol, nonylphenol, alkylphenol polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusting agents can be prepared by mixing or milling the active ingredients together with a solid carrier.

The formulations contain in general from 0.01 to 95, preferably from 0.1 to 90, % by weight of the active ingredient. The active ingredients are used in a purity of from 90 to 100%, preferably from 95 to 100% (according to the NMR spectrum).

Examples of formulations are:

I. 5 parts by weight of compound No. 3.1 are thoroughly mixed with 95 parts by weight of finely divided kaolin. A dusting agent which contains 5% by weight of the active ingredient is obtained in this manner.

II. 30 parts by weight of compound No. 3.1 are thoroughly mixed with a mixture of 92 parts by weight of silica gel powder and 8 parts by weight of liquid paraffin, which were sprayed onto the surface of this silica gel. A formulation of the active ingredient having good adhesion (active ingredient content 23% by weight) is obtained in this manner.

III. 10 parts by weight of compound No. 3.2 are dissolved in a mixture which consists of 90 parts by weight of xylene, 6 parts by weight of the adduct of from 8 to 10 mol of ethylene oxide with 1 mol of N-monoethanololeamide, 2 parts by weight of the calcium salt of dodecylbenzenesulfonic acid and 2 parts by weight of the adduct of 40 mol of ethylene oxide with 1 mol of castor oil (active ingredient content 9% by weight).

IV. 20 parts by weight of compound No. 3.1 are dissolved in a mixture which consists of 60 parts by weight of cyclohexanone, 30 parts by weight of isobutanol, 5 parts by weight of the adduct of 7 mol of ethylene oxide with 1 mol of isooctylphenol and 5 parts by weight of the adduct of 40 mol of ethylene oxide with 1 mol of castor oil (active ingredient content 16% by weight).

V. 80 parts by weight of compound No. 3.2 are thoroughly mixed with 3 parts by weight of the sodium salt of diisobutylnaphthalene-alphasulfonic acid, 10 parts by weight of the sodium salt of ligninsulfonic acid obtained from a sulfite waste liquor and 7 parts by weight of silica gel powder, and the mixture is milled in a hammer mill (active ingredient content 80% by weight).

VI. 90 parts by weight of compound No. 3.2 are mixed with 10 parts by weight of N-methyl-α-pyrrolidone, and a solution which is suitable for use in the form of very small drops is obtained (active ingredient content 90% by weight).

VII. 20 parts by weight of compound No. 3.1 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

VIII. 20 parts by weight of active ingredient No. 3.2 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

Granules, for example coated, impregnated and homogeneous granules, can be prepared by binding the active ingredient to solid carriers. Examples of solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, e.g. ammonium sulfate, ammonium phosphate, ammonium nitrate and ureas, and vegetable products, such as grain flours, bark meal, wood meal and nutshell meal, cellulosic powders and other solid carriers.

The active ingredient concentrations in the ready-to-use formulations can be varied within relatively wide ranges.

In general, they are from 0.0001 to 10%, preferably from 0.01 to 1%.

The active ingredients can also be successfully used by the ultralow volume (ULV) method, it being possible to apply formulations containing more than 95% by weight of active ingredient or even the active ingredient without additives.

The application rate of active ingredient under open air conditions is from 0.01 to 10, preferably from 0.1 to 1, kg/ha.

Oils of various types, herbicides, fungicides, other pesticides and bactericides may be added to the active ingredients, if necessary directly before use (tank mix). These agents can be mixed with the novel agents in a weight ratio of from 1:10 to 10:1.

SYNTHESIS EXAMPLES

The methods described in the Synthesis Examples below were used with appropriate modification of the starting compounds for obtaining further compounds Ia and Ib. The compounds thus obtained are listed with physical data in the Tables below.

Preparation of starting materials 1. 3-Amino-2-methylbenzyl alcohol

A solution of 203 g of 2-methyl-3-nitrobenzyl alcohol in 1000 ml of ethanol is hydrogenated in the presence of 5 g of 10% strength Pd/carbon at from 30 to 35° C. The catalyst is filtered off, the solution is evaporated down and the resulting solid is dried. 145 g of 3-amino-2-methylbenzyl alcohol (mp. 104°–108° C.) are obtained.

2. 3-Bromo-2-methylbenzyl alcohol

A solution of 40.7 g of sodium nitrate in 300 ml of water is added dropwise to a mixture, cooled to 0° C., of 888 ml of water, 162 ml of 47% hydrobromic acid and 81.2 g of 3-amino-2-methylbenzyl alcohol. Stirring is carried out for 30 minutes at 0° C., after which a suspension of 168.7 9 of copper(I) bromide in 750 ml of water is added a little at a time at this temperature. The reaction mixture is stirred in succession for 1 hour at 10° C., for 1 hour at room temperature and for 2 hours at 100° C. After cooling, the reaction mixture is extracted several times with ether. The combined organic phases are washed with water, dried and evaporated down. Purification by column chromatogrpahy over silica gel using toluene as the mobile phase gives 64.2 g of 3-bromo-2-methylbenzyl alcohol (mp. 97°–100° C.).

3. 3-Bromo-2-methylbenzyl tetrahydro-2-pyranyl ether 2.1 ml of concentrated hydrochloric acid are added at 0° C. to a solution of 208.9 g of 3-bromo-2-mathylbenzyl alcohol and 87.4 g of 3,4-dihydro-2H-pyran in 1600 ml of ether. Stirring is carried out for 4 days at room temperature, after which 50 ml of 10% strength potassium hydroxide solution in 500 ml of water are added dropwise at room temperature. The organic phase is separated off, the aqueous phase is extracted with ether and the combined organic phases are washed with water, dried and evaporated down. Purification by column chromatography over silica gel using toluene as the mobile phase gives 224.6 g of the desired compound.

NMR spectrum [300 MHz; CDCl$_3$; δ(ppm)]: 1.4–1.91 (6H); 2.42 (3H); 3.55 (1H); 3.89 (1H); 4.47 (1H); 4.68 (1H); 4.8 (1H); 7.02 (1H); 7.32 (1H); 7.47 (1H).

4. 3-Formyl-2-methylbenzyl tetrahydro-2-pyranyl ether 1.2 g of Mg (magnesium shavings) in 15 ml of absolute tetrahydrofuran are initially introduced under a nitrogen atomsphere. A few drops of dibromomethane are added at 65° C. A solution of 14.25 g of 3-bromo-2-methylbenzyl tetrahydro-2-pyranyl ether in 50 ml of tetrahydrofuran is added dropwise while the temperature is kept at 65° C. The refluxed mixture is then stirred for 2 hours. A solution of 5.65 g of N-formylpiperidine in 10 ml of absolute tetrahydrofuran is added dropwise to the reaction mixture after the latter has been cooled to 0° C. Stirring is carried out for 20 hours at room temperature, the mixture is rendered slightly acidic with about 50 ml of 5% strength hydrochloric acid and extraction is carried out several times with ether. The combined ether extracts are washed with water, dried and evaporated down. The crude product (11 g) can be purified by column chromatography over silica gel using 97.5:2.5 toluene/acetone.

NMR spectrum [2500 MHz; CDCl$_3$; δ(ppm)]: 1.48–1.93 (6H); 2.64 (3H); 3.57 (1H); 3.9 (1H); 4.54 (1H); 4.72 (1H); 4.86 (1H); 7.36 (1H); 7.65 (1H); 7.76 (1H); 10.33 (1H).

5. 3-(2',2'-Dibromovinyl)-2-methylbenzyl tetrahydro-2-pyranyl ether

A solution of 41.44 g of tetrabromomethane in 40 ml of methylene chloride is added dropise at 0° C. to a solution of 64.85 g of triphenylphosphine in 60 ml of methylene chloride. Stirring is carried out for 30 minutes at 0° C., after which 23.1 g of 3-formyl-2-methylbenzyl tetrahydro-2-pyranyl ether in 25 ml of methylene chloride are added dropwise. After stirring has been carried out for 2 hours at room temperature, the solid is filtered off and the filtrate is evaporated down. 200 ml of cyclohexane and 200 ml of water are added to the filtrate. The refluxed mixture is stirred for 1 hour and the organic phase is separated off, dried and evaporated down. Purification by column chromatography over silica gel using cyclohexane and toluene as the mobile phase gives 4 g of 3-(2',2'-dibromovinyl)-2-methylbenzyl bromide and 18.4 g of the desired compound.

NMR spectrum [300 MHz; CDCl₃; δ(ppm)]: 1.48–1.92 (6H); 2.23 (3H); 3.55 (1H); 3.9 (1H); 4.48 (1H); 4.72 (1H); 4.81 (1H); 7.19 (1H); 7.28 (1H); 7.38 (1H); 7.5 (1H).

6. 3-(2',2'-Dichlorovinyl)-2-methylbenzyl tetrahydro-2-pyranyl ether

Method A 7.86 g of triphenylphosphine are added rapidly at 0°–5° C. to a suspension of 3.37 g of potassium tertbutylate butylate in 50 ml of heptane under a nitrogen atmosphere. 3.59 g of chloroform in 30 ml of heptane are then added dropwise in the course of 1 hour, likewise at 0°–5° C. The resulting tert-butanol is distilled off at 0° C. under reduced pressure. A solution of 7.02 g of 3-formyl-2-methylbenzyl tetrahydro-2-pyranyl ether in 10 ml of heptane is added dropwise at 5°–10° C. in the course of 30 minutes and stirring is carried out for 2 hours at 5° C. and 15 hours at room temperature. The precipitated solid is filtered off and the solution is evaporated down. Purification by column chromatography over silica gel using toluene as the mobile phase gives 2.3 g of the desired ether.

Method B 33.1 ml (0.053 mol) of n-butyllithium (15% strength solution in hexane) and then 11.7 g of 3-formyl-2-methylbenzyl tetrahydro-2-pyranyl ether in 10 ml of 1:1 ether/tetrahydrofuran are added dropwise at −100° C. to a solution of 12.8 g of diethyl trichloromethylphosphonate in 45 ml of ether and 35 ml of tetrahydrofuran under a nitrogen atmosphere. The mixture is allowed to warm up to room temperature while stirring and is refluxed for 1 hour. The reaction mixture is cooled to −50° C., 50 ml of 2N sulfuric acid are added and the mixture is poured into 300 ml of water and extracted several times with ether. The combined ether phases are washed with water, dried and evaporated down. Purification by column chromatography over silica gel using toluene as the mobile phase gives 4.7 g of the desired compound.

NMR spectrum [300 MHz; CDCl₃; δ(ppm)]: 1.47–1.93 (6H); 2.25 (3H); 3.57 (1H); 3.92 (1H); 4.48 (1H); 4.72 (1H); 4.81 (1H); 6.95 (1H); 7.2 (1H); 7.35 (2H).

1. Synthesis of the 3-isoxazolylbenzyl derivatives XVa 1.1 3-Isoxazol-3'-yl-2-methylbenzyl alcohol

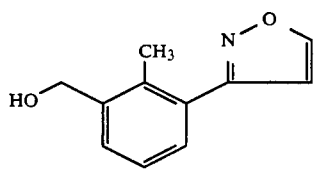

A 3-Hydroximinomethyl-2-methylbenzyl tetrahydro-2-pyranyl ether

A solution of 2.67 g of hydroxylamine hydrochloride and 10 ml of water was added at 25° C. to a solution of 6.0 g of 3-formyl-2-methylbenzyl tetrahydro-2-pyranyl ether and 50 ml of toluene. After the addition of 2.01 g of sodium carbonate in 10 ml of H₂O, stirring was carried out overnight at 25° C. The product which crystallized out in the course of the reaction was filtered off and dissolved in ether. 6.4 g of product were obtained from the combined organic phases after washing and drying.

NMR spectrum [300 MHz; CDCl₃; δ(ppm)]: 1.2–1.85 (6H); 2.32 (3H); 3.50 (1H); 3.78 (1H); 4.40–4.85 (3H); 7.05–7.7 (3H); 8.42 (1H); 11.27 (1H).

B 3-Isoxazol-3'-yl-2-methylbenzyl tetrahydro-2-pyranyl ether

Acetylene was passed into a solution of 6.23 g of 3-hydroximinomethyl-2-methylbenzyl tetrahydro-2-pyranyl ether and 50 ml of CH₂Cl₂ at from 0° to 5° C. in the course of 30 minutes. 20.6 ml of a 10% strength sodium hypochlorite solution to which a pinch of sodium acetate had been added were then introduced dropwise at 10° C. with further passage of acetylene. After the end of the addition, acetylene was passed in for a further 15 minutes at 10° C. Stirring was then carried out for 1 hour at 10° C. After 14 hours at 25° C., the two phases were separated. 4.8 g of product were obtained from the organic phase after washing, drying and purification by column chromatography (silica gel; 97.5:2.5 toluene/acetone).

NMR spectrum [250 MHz; CDCl₃; δ(ppm)]1.40–2.0 (6H); 2.38 (3H); 3.55 (1H); 3.92 (1H); 4.45–4.90 (3H); 6.48 (1H); 7.20–7.50 (3H); 8.43 (1H).

C 4.7 g of 3-isoxazol-3'-yl-2-methylbenzyl tetrahydro-2-pyranyl ether, dissolved in 40 ml of methanol, were stirred with 2.72 ml of concentrated hydrochloric acid for 14 hours at 25° C. Neutralization was then effected with sodium methylate solution while cooling with ice, and the neutral solution was evaporated down under reduced pressure. Water was added to the residue, and the solution was extracted several times with diethyl ether. 3.0 g of 3-isoxazol-3'-yl-2-methylbenzyl alcohol were obtained from the combined ether extracts.

NMR spectrum [300 MHz; CDCl₃; δ(ppm)]: 2.25 (3H); 2.70 (1H); 4.65 (2H); 6.43 (1H); 7.15–7.50 (3H); 8.27 (1H).

2. Synthesis of the 3-isoxazolylbenzyl derivatives XVb 2.1 3-(3'-Ethylisoxazol-5'-yl)-2-methylbenzyl alcohol

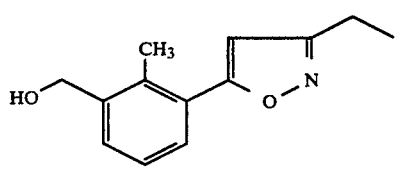

A 3-Ethynyl-2-methylbenzyl tetrahydro-2-pyranyl ether 19.7 ml of a 1.6 molar solution of n-butyllithium in n-hexane were added at −78° C. to a solution of 5.85 g of 3-(2',2'-dibromovinyl)-2-methylbenzyl tetrahydro-2- pyranyl ether and 50 ml of tetrahydrofuran. After 1 hour at −78° C., followed by 1 hour at 25° C., the reaction solution was added to 300 ml of ice water. The mixture thus obtained was extracted with diethyl ether. 3.1 g of the product (80% pure according to NMR) were obtained from the combined organic phases after washing, drying and purification by chromatography (silica gel, toluene).

NMR spectrum [200 MHz; CDCl$_3$; δ(ppm)]1.40–2.00 (6H); 2.48 (3H); 3.30 (1H); 3.60 (1H); 3.95 (1H); 4.40–4.95 (3H); 7.1–7.55 (3H).

B 3-(3'-Ethylisoxazol-5'-yl)-2-methylbenzyl tetrahydro-2-pyranyl ether

A solution of 3.43 g of nitropropane and 10 ml of toluene, and 3 drops of triethylamine, were added to a mixture of 9.2 g of phenyl isocyanate, 10.6 g of 3-ethynyl-2-methylbenzyl tetrahydro-2-pyranyl ether and 20 ml of toluene at 25° C. After 14 hours at 25° C., the mixture was heated for 2 hours at 100° C. After cooling to 25° C., the reaction mixture was freed from solid components. 2.3 g of the product were obtained from the resulting solution after chromatography [silica gel; 98:2 toluene/acetone].

NMR spectrum [300 MHz; CDCl$_3$; δ(ppm)]: 1.36 (3H); 1.42–1.95 (6H); 2.21 (3H); 2.75 (2H); 3.55 (1H); 3.92 (1H); 4.4–4.9 (3H); 6.23 (1H); 7.0–7.6 (3H).

C 2.3 g of 3-(3'-ethylisoxazol-5'-yl)-2-methylbenzyl tetrahydro-2-pyranyl ether, dissolved in 40 ml of methanol, were stirred with 1.22 ml of concentrated hydrochloric acid for 14 hours at 25° C. Thereafter, neutralization was effected with sodium methylate solution while cooling with ice and the neutral solution was evaporated down under reduced pressure. Water was added to the residue, and the solution was extracted several times with diethyl ether. 1.4 g of 3-(3'-ethylisoxazol-5'-yl)-2-methylbenzyl alcohol were obtained from the combined ether extracts.

NMR spectrum [300 MHz; CDCl$_3$; δ(ppm)]: 1.33 (2H); 2.37 (3H); 3.75 (2H); 4.72 (2H); 6.21 (1H); 7.2–7.6 (3H).

3. Synthesis of 3-isoxazolylphenyl derivatives Ia and Ib 3.1 Preparation of dimethyl-3-(2'-methyl-3'-(3''-isoxazolyl)-phenyl)-propylphenylsilane 3.1.1 1-Chloro-2-methyl-3-prop-2-enylbenzene 158 g of vanadium trichloride are dissolved in 800 ml of dichloromethane, and 500 ml of a solution of 1 mol of 2-methyl-3-chlorophenylmagnesium chloride in THF are added at 25° C. Stirring is carried out for 0.5 hour, after which 121 g of allyl bromide are added dropwise, stirring is effected for 10 hours at 25° C. and the mixture is then refluxed for 6 hours. The resulting reaction mixture is poured into 2 l of saturated, aqueous sodium bicarbonate solution and then extracted with methyl tertbutyl ether. 70.9 g of 1-chloro-2-methyl-3-prop-2-enylbenzene (bp. 78° C./1 mbar) are obtained by distillation.

3.1.2 1-Cyano-2-methyl-3-prop-2-enylbenzene 30 g of 1-chloro-2-methyl-3-prop-2-enylbenzene are dissolved in 150 ml of N-methylpyrrolidone, and 25 g of copper(I) cyanide are added. The reaction mixture is heated at 190° C. for 30 hours while stirring. After the mixture has been cooled to 20° C., 125 ml of ethylenediamine and 300 ml of water are added. Stirring is then carried out for 1 hour at 50° C. and for 14 hours at 20° C. Working up is effected by extracting with diethyl ether, washing the organic phase and drying over sodium sulfate, removing the drying agent and distilling off the organic solvent. 24.5 g of crude product are obtained. After chromatography (silica gel/toluene), 14.4 g of pure 1-cyano-2-mehtyl-3-prop-2-enylbenzene are isolated.

$^1$H-NMR [300 MHz; CDCl$_3$; δ(ppm)]: 2.45 (3H); 3.40 (2H); 4.9–5.1 (2H); 5.9 (1H); 7.1–7.4 (3H).

3.1.3 Dimethyl-3-(2'-methyl-3'-cyanophenyl)-propylphenylsilane 9.0 g of 1-cyano-2-methyl-3-prop-2-enylbenzene are dissolved in 100 ml of absolute cyclohexane, and 7.75 g of dimethylphenylsilane are added at room temperature. 0.1 g of hexachloroplatinic acid hexahydrate, dissolved in 2 ml of absolute isopropanol, is added to this mixture. The reaction mixture is stirred for 3 hours at 55° C. The solvent is removed by distillation in a rotary evaporator. High boiling components are separated off by distillation under reduced pressure (condensate 82°–105° C./0.1 mbar). The residue is purified by column chromatography (silica gel/toluene). 12.2 g of dimethyl-3-(2'-methyl-3'-cyanophenyl)-propylphenylsilane are obtained.

$^1$H-NMR [300 MHz; CDCl$_3$; δ(ppm)]: 0.25 (6H); 0.8 (2H); 1.55 (2H); 2.4 (3H); 2.6 (2H); 7.1–7.6 (8H).

3.1.4 Dimethyl-3-(2'-methyl-3-formylphenyl)-propylphenylsilane 11 g of dimethyl-3-(2'-methyl-3'-cyanophenyl)-propylphenylsilane are dissolved in 100 ml of absolute toluene, and 28 ml of a 25% strength solution of diisobutylaluminum hydride in toluene are added slowly at 20° C. under nitrogen. Refluxing is carried out for 6 hours, after which first 3 ml of methanol and then 50 ml of 10% strength hydrochloric acid are added at 20° C. The reaction mixture is stirred for 14 hours at 20° C. After phase separation, the organic phase is washed with distilled water, dried over Na$_2$SO$_4$, filtered and then freed from adhering solvents by means of a rotary evaporator and a vacuum pump.

10.2 g of dimethyl-3-(2'-methyl-3'-formylphenyl)-propylphenylsilane are obtained.

$^1$H-NMR [300 MHz; CDCl$_3$; δ(ppm)]: 0.25 (6H); 0.85 (2H); 1.55 (2H); 2.58 (3H); 2.7 (2H); 7.2–7.7 (8H); 10.3 (1H).

3.1.5 Dimethyl-3-(2'-methyl-3'-(2''-hydroximinomethyl)-phenyl)-propylphenylsilane 10.1 g of dimethyl-3-(2'-methyl-3'-formylphenyl)-propylphenylsilane are dissolved in 150 ml of toluene, and a solution of 3.42 g of hydroxylamine hydrochloride in 30 ml of water is added at 20° C.

A solution of 2.65 g of sodium carbonate in 30 ml of water is then added dropwise. The reaction mixture is stirred vigorously for 14 hours at 20° C. After phase separation, the organic phase is washed with water, dried over sodium sulfate, filtered and finally freed from the solvent in a rotary evaporator. The remaining residue is purified by column chromatography (silica gel; 95:5 toluene/acetone). 7.0 g of dimethyl-3-(2'-methyl-3'-(2''-hydroximinomethyl)-phenyl) -propylphenylsilane are obtained.

¹H-NMR [300 MHz; CDCl₃; δ(ppm)]: 0.25 (6H); 0.8 (2H); 1.55 (2H); 2.25 (3H); 2.6 (2H); 7.0–7.6 (8H); 8.5 (1H); 9.1 (1H).

3.1.6
Dimethyl-3-(2'-methyl-3'-(3''-isoxazolyl)phenyl)-propylphenylsilane 2.6 g of dimethyl-3-(2'-methyl-3'-(2''-hydroximinomethyl)-phenyl)-propylphenylsilane are dissolved in 70 ml of dichloromethane. Acetylene is passed into this solution at 0° C. for 0.5 hour while stirring vigorously. Without interrupting the passage of acetylene, 7.0 ml of a 10% strength sodium hypochlorite (to which 0.5 g of sodium acetate has been added) are then added dropwise in the course of 0.3 hour. Acetylene is then passed in for a further 0.5 hour. The reaction mixture is stirred vigorously for 14 hours while slowly warming up to 20° C. After the addition of 70 ml of dichloromethane, the phases are separated. The organic phase is washed twice with water, dried over sodium sulfate, filtered and freed from the solvent in a rotary evaporator. The remaining residue is purified by chromatography (silica gel; 95:5 petroleum ether/methyl tert-butyl ether). 1.8 g of dimethyl-3-(2'-methyl-3'-(3''-isoxazolyl)-phenyl)-propylphenylsilane are isolated.

¹H-NMR [360 MHz; CDCl₃; δ(ppm)]: 0.25 (6H); 0.85 (2H); 1.6 (2H); 2.3 (3H); 2.7 (2H); 6.5 (1H); 7.15–7.5 (7H); 8.4 (1H).

3.2 Preparation of dimethyl-3-(2'-methyl-3'-(3''-isoxazolyl)-phenyl)-propyl-(4'-ethoxyphenyl)-silane

3.2.1 Dimethyl-(4-ethoxyphenyl)-chlorosilane 12 g of magnesium turnings are covered with a layer of absolute tetrahydrofuran. First, a solution of 100.5 g of 4-ethoxybromobenzene in 100 ml of absolute tetrahydrofuran is slowly added dropwise with gentle heating. After the beginning of the exothermic formation of the Grignard reagent, the dropwise addition is effected so rapidly that the reaction mixture boils by itself. Refluxing is carried out for 1 hour after the addition is complete. The Grignard solution thus obtained is cooled to 20° C. and added dropwise to a solution of 129 g of dichloromethylsilane in 100 ml of absolute tetrahydrofuran in the course of 1 hour at 0° C. After the end of the addition, the mixture is allowed to warm up to 20° C. and is then refluxed for 1 hour. Thereafter, it is cooled to 20° C. and filtered off from the residue. The residue is washed with tetrahydrofuran. The combined organic phases are evaporated down at 760 mbar. 156 g of a dark oil are obtained. Double distillation of the oil gives 54.4 g (bp. 99° C./0.4 mbar) of dimethyl-(4-ethoxyphenyl)-chlorosilane.

3.2.2 Dimethyl-(4-ethoxyphenyl)-silane

A solution of 51 g of dimethyl-(4-ethoxyphenyl)-chlorosilane in 100 ml of absolute diethyl ether is added dropwise to a suspension of 2.55 g of lithium aluminum hydride in 30 ml of absolute diethyl ether under nitrogen at 15°-20° C. Stirring is carried out for 1 hour at 20° C., followed by refluxing for 1 hour. The reaction solution is cooled to 20° C. and poured into 200 ml of 2N sulfuric acid. The phases are separated and, after the aqueous phase has been washed several times with diethyl ether, the organic phases are combined and are evaporated down in a rotary evaporator. Distillation of the residue gives 29.0 g of dimethyl-(4-ethoxyphenyl)-silane (bp. 53° C./0.2 mbar).

3.2.3 Dimethyl-3-(2'-methyl-3'-cyanophenyl)-propyl-(4'-ethoxyphenyl)-silane Preparation similar to Example 3.1.3

¹H-NMR [200 MHz; CDCl₃; δ(ppm)]0.22 (6H); 0.8 (2H); 1.4 (3H); 1.55 (2H); 2.4 (3H); 2.55 (2H); 4.0 (2H); 6.8–7.4 (7H).

3.2.4 Dimethyl-3-(2'-methyl-3'-formylphenyl)propyl-(4'-ethoxyphenyl)-silane Preparation similar to Example 3.1.4

¹H-NMR [360 MHz; CDCl₃; δ(ppm)]: 0.2 (6H); 0.75 (2H); 1.4 (3H); 1.6 (2H); 2.5 (3H); 2.75 (2H); 4.0 (2H); 6.8–7.6 (7H); 10.25 (1H).

3.2.5 Dimethyl-3-(2'-methyl-3'-(2''-hydroximinomethyl)-phenyl)propyl-(4'-ethoxyphenyl)-silane Preparation similar to Example 3.1.5

¹H-NMR [200 MHz; CDCl₃; δ(ppm)]: 0.25 (6H); 0.8 (2H); 1.4 (3H); 1.75 (2H); 2.2 (3H); 2.6 (2H); 4.0 (2H); 6.8–7.6 (7H); 8.45 (1H); 9.3 (1H).

3.2.6 Dimethyl-3-(2'-methyl-3'-(3''-isoxazolyl)-phenyl)propyl-(4'-ethoxyphenyl)-silane Preparation similar to Example 3.1.6

¹H-NMR [270 MHz; CDCl₃; δ(ppm)]: 0.25 (6H); 0.8 (2H); 1.35 (3H); 1.6 (2H); 2.25 (3H); 2.65 (2H); 4.0 (2H); 6.4 (1H); 6.8–7.35 (7H); 8.4 (1H).

Use Examples

The insecticidal activity of the 3-isoxazolylphenyl compounds of the general formula Ia and Ib could be demonstrated by the following experiments:

The active ingredients were prepared
a) as a 0.1% strength solution in acetone or
b) as a 10% strength emulsion in a mixture of 70% by weight of cyclohexanol, 20% by weight of Nekanil ® LN (Lutensol ® AP6, wetting agent having an emulsifying and dispersing action and based on ethoxylated alkylphenol) and 10% by weight of Emulphor ® EL (Emulan ® EL, emulsifier based on ethoxylated fatty alcohols)

and were diluted with acetone in the case of a) and with water in the case of b) to give the desired concentration.

*Nephotettix cineticeps* (rice cicada), contact action

Rice plants about 8 cm high were treated with aqueous formulations of the active ingredients; subsequently, 10 adult cicadas were placed on the plants. The kill rate was assessed after 48 hours as follows:

100% = no surviving cicadas;
80% = 1–2 survivors;
60% = 3–4 survivors;
0% = more than 4 survivors.

In this test, application of 200 ppm of the compound of Example 3.2 resulted in a 100% action.

We claim:
1. A 3-isoxazolylphenyl compound of the formula Ia or Ib

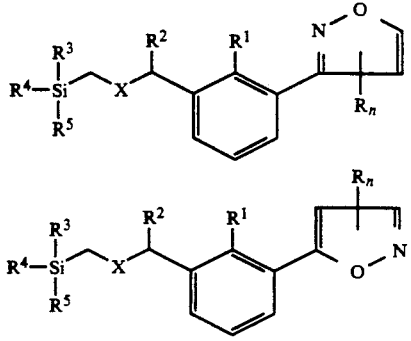

where
R is halogen; $C_1$-$C_4$-alkyl; $C_1$-$C_4$-haloalkyl; $C_1$-$C_4$-alkoxy; $C_1$-$C_4$-haloalkoxy; $C_2$-$C_4$-alkenyl; $C_2$-$C_4$-haloalkenyl;
phenylethenyl which may carry from one to five halogen atoms;
$C_2$-$C_4$-alkynyl; $C_3$-$C_8$-cycloalkyl; aryl; hetaryl; $CO_2R^6$ or $CONR^7R^8$,
where $R^6$ is hydrogen, $C_1$-$C_6$-alkyl, $C_3$-$C_5$-cycloalkyl or benzyl and
$R^7$ and $R^8$ independently of one another are each hydrogen, $C_1$-$C_6$-alkyl, $C_3$-$C_6$-cycloalkyl or benzyl or, together with the nitrogen atom to which they are bonded, form a 3-membered to 8-membered, saturated or monounsaturated or diunsaturated heterocyclic radical consisting of carbon ring members, where this cyclic structure may furthermore contain one or two further hetero atoms selected from the group consisting of oxygen, sulfur and nitrogen;
n is 0, 1 or 2, and the radicals R may be different when n is 2;
$R^1$ is halogen or $C_1$-$C_4$-alkyl;
$R^2$ is hydrogen; $C_1$-$C_4$-alkyl; $C_2$-$C_4$-alkenyl; $C_2$-$C_4$-alkynyl or cyano;
$R^3$ and $R^4$ independently of one another are each $C_1$-$C_4$-alkyl or $C_2$-$C_8$-alkenyl, where these radicals may carry from one to nine halogen atoms or one of the following groups:
$C_3$-$C_8$-cycloalkyl, $C_1$-$C_4$-alkoxy, $C_1$-$C_4$-haloalkoxy, $C_1$-$C_4$-alkylthio, $C_1$-$C_4$-haloalkylthio, phenyl, phenoxy and phenylthio, and the aromatic groups in turn may carry from one to five halogen atoms or from one to three of the following $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;
$C_3$-$C_8$-cycloalkyl which may carry from one to three of the following groups: halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;
phenyl, naphthyl, pyridyl or pyrimidyl, where the aromatic radicals may carry from one to seven halogen atoms or from one to four of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;
or $R^3$ and $R^4$ together form $C_2$-$C_5$-alkylene which may carry from one to three $C_1$-$C_3$-alkyl groups;
$R^5$ is hydrogen;
$C_5$-$C_{18}$-alkyl which may carry from one to nine halogen atoms or one of the following groups: $C_3$-$C_8$-cycloalkyl, $C_1$-$C_4$-alkoxy, $C_1$-$C_4$-haloalkoxy, $C_1$-$C_4$-alkylthio, $C_1$-$C_4$-haloalkylthio, phenyl, phenoxy and phenylthio, where the aromatic groups in turn may carry from one to five halogen atoms or from one to three of the following groups $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio; or one of the groups stated for $R^3$;
X is $CH_2$, O, S or $NR^9$, where
$R^9$ is hydrogen, $C_1$-$C_4$-alkyl, $C_3$-$C_6$-cycloalkyl, $C_2$-$C_4$-alkenyl, $C_2$-$C_4$-alkynyl or benzyl, and the benzyl radical in turn may carry from one to five halogen atoms or from one to three of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio.

2. A 3-isoxazolylphenyl compound of the formula Ia or Ib as claimed in claim 1, wherein $R^1$ is methyl or ethyl and $R^2$ is hydrogen.

3. A 3-isoxazolylphenyl compound of the formula Ia or Ib as claimed in claim 1, wherein $R^1$ is methyl or ethyl, $R^2$ is hydrogen and n is 0.

4. A 3-isoxazolylphenyl compound of the formula Ia or Ib as claimed in claim 1, wherein $R^5$ is hydrogen or methyl and $R^4$ is methyl or cyclopropyl.

5. A 3-isoxazolylphenyl compound of the formula Ia or Ib as claimed in claim 1, wherein $R^3$ is phenyl, pyridyl or pyrimidinyl, where the aromatic radicals may carry from one to five halogen atoms or from one to three of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio.

6. A 3-isoxazolylphenyl compound of the formula Ia or Ib as claimed in claim 1, wherein $R^5$ is hydrogen or methyl, $R^4$ is methyl or cyclopropyl and $R^3$ is phenyl, pyridyl or pyrimidinyl, where the aromatic radicals may carry from one to five halogen atoms or from one to three of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio.

7. A pesticide containing a 3-isoxazolylphenyl compound of the formula Ia or Ib as claimed in claim 1 and inert additives.

8. A method for controlling pests, wherein the pests or their habitat is or are treated with an effective amount of a 3-isoxazolylphenyl compound of the formula Ia or Ib as claimed in claim 1.

* * * * *